(12) United States Patent
Wolf et al.

(10) Patent No.: US 12,201,384 B2
(45) Date of Patent: *Jan. 21, 2025

(54) TRACKING SYSTEMS AND METHODS FOR IMAGE-GUIDED SURGERY

(71) Applicant: AUGMEDICS LTD., Yokneam Illit (IL)

(72) Inventors: Stuart Wolf, Yokneam (IL); Nissan Elimelech, Beerotaim (IL)

(73) Assignee: AUGMEDICS LTD., Yokneam Illit (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/631,877

(22) Filed: Apr. 10, 2024

(65) Prior Publication Data
US 2024/0341861 A1 Oct. 17, 2024

Related U.S. Application Data

(63) Continuation of application No. 18/470,809, filed on Sep. 20, 2023, now Pat. No. 11,980,429, which is a
(Continued)

(51) Int. Cl.
*A61B 34/20* (2016.01)
*A61B 34/00* (2016.01)
(Continued)

(52) U.S. Cl.
CPC .............. *A61B 34/20* (2016.02); *A61B 34/25* (2016.02); *A61B 90/36* (2016.02);
(Continued)

(58) Field of Classification Search
None
See application file for complete search history.

(56) References Cited

U.S. PATENT DOCUMENTS

| | | | |
|---|---|---|---|
| 3,101,715 A | 8/1963 | Glassman |
| 3,690,776 A | 9/1972 | Zaporoshan |

(Continued)

FOREIGN PATENT DOCUMENTS

| | | | |
|---|---|---|---|
| CA | 3022448 A1 | 2/2018 |
| CA | 3034314 A1 | 2/2018 |

(Continued)

OTHER PUBLICATIONS

U.S. Appl. No. 15/896,102 U.S. Pat. No. 10,134,166, filed Feb. 14, 2018 Nov. 20, 2018, Combining Video-based and Optic-based Augmented Reality in a Near Eye Display.
(Continued)

*Primary Examiner* — Serkan Akar
*Assistant Examiner* — Farouk A Bruce
(74) *Attorney, Agent, or Firm* — KNOBBE, MARTENS, OLSON & BEAR, LLP

(57) ABSTRACT

Apparatus and methods are described including tracking a tool portion and a patient marker from a first line of sight, using a first tracking device disposed upon a first head-mounted device that includes a display. The tool portion and the patient marker are tracked from a second line of sight, using a second tracking device. When a portion of the patient marker and the tool portion are both within the first line of sight, an augmented reality image is generated upon the first display based upon data received from the first tracking device and without using data from the second tracking device. When at least the patient marker portion and the tool portion are not both within the first line of sight, a virtual image of the tool and anatomy of the patient is generated using data received from the second tracking device. Other applications are also described.

20 Claims, 6 Drawing Sheets

Related U.S. Application Data continuation of application No. 16/200,144, filed on Nov. 26, 2018, now Pat. No. 11,766,296.

(51) Int. Cl.
*A61B 34/10* (2016.01)
*A61B 90/00* (2016.01)
*G02B 27/00* (2006.01)
*G02B 27/01* (2006.01)

(52) U.S. Cl.
CPC ..... *G02B 27/0093* (2013.01); *G02B 27/0172* (2013.01); *A61B 34/10* (2016.02); *A61B 2034/2055* (2016.02); *A61B 2090/365* (2016.02); *G02B 2027/0178* (2013.01)

(56) References Cited

U.S. PATENT DOCUMENTS

| | | |
|---|---|---|
| 4,459,358 A | 7/1984 | Berke |
| 4,711,512 A | 12/1987 | Upatnieks |
| 4,863,238 A | 9/1989 | Brewster |
| 4,944,739 A | 7/1990 | Torre |
| 5,100,420 A | 3/1992 | Green et al. |
| 5,147,365 A | 9/1992 | Whitlock et al. |
| 5,357,292 A | 10/1994 | Wiedner |
| 5,410,802 A | 5/1995 | Buckley |
| 5,441,042 A | 8/1995 | Putman |
| 5,442,146 A | 8/1995 | Bell et al. |
| 5,510,832 A | 4/1996 | Garcia |
| D370,309 S | 5/1996 | Stucky |
| 5,620,188 A | 4/1997 | McCurry et al. |
| 5,636,255 A | 6/1997 | Ellis |
| 5,665,092 A | 9/1997 | Mangiardi et al. |
| 5,743,731 A | 4/1998 | Lares et al. |
| 5,771,121 A | 6/1998 | Hentschke |
| 5,792,046 A | 8/1998 | Dobrovolny |
| 5,841,507 A | 11/1998 | Barnes |
| 6,006,126 A | 12/1999 | Cosman |
| 6,038,467 A | 3/2000 | De Bliek et al. |
| 6,125,164 A | 9/2000 | Murphy et al. |
| 6,138,530 A | 10/2000 | McClure |
| 6,147,805 A | 11/2000 | Fergason |
| 6,227,667 B1 | 5/2001 | Halldorsson et al. |
| 6,256,529 B1 | 7/2001 | Holupka et al. |
| 6,285,505 B1 | 9/2001 | Melville et al. |
| 6,314,310 B1 | 11/2001 | Ben-Haim et al. |
| 6,349,001 B1 | 2/2002 | Spitzer |
| 6,444,192 B1 | 9/2002 | Mattrey |
| 6,447,503 B1 | 9/2002 | Wynne et al. |
| 6,449,090 B1 | 9/2002 | Omar et al. |
| 6,456,405 B2 | 9/2002 | Horikoshi et al. |
| 6,456,868 B2 | 9/2002 | Saito et al. |
| 6,474,159 B1 | 11/2002 | Foxlin et al. |
| 6,518,939 B1 | 2/2003 | Kikuchi |
| 6,527,777 B2 | 3/2003 | Justin |
| 6,529,331 B2 | 3/2003 | Massof et al. |
| 6,549,645 B1 | 4/2003 | Oikawa et al. |
| 6,578,962 B1 | 6/2003 | Amir et al. |
| 6,609,022 B2 | 8/2003 | Vilsmeier et al. |
| 6,610,009 B2 | 8/2003 | Person |
| D480,476 S | 10/2003 | Martinson et al. |
| 6,659,611 B2 | 12/2003 | Amir et al. |
| 6,675,040 B1 | 1/2004 | Cosman |
| 6,683,584 B2 | 1/2004 | Ronzani et al. |
| 6,690,964 B2 | 2/2004 | Bieger et al. |
| 6,714,810 B2 | 3/2004 | Grzeszczuk et al. |
| 6,737,425 B1 | 5/2004 | Yamamoto et al. |
| 6,740,882 B2 | 5/2004 | Weinberg |
| 6,757,068 B2 | 6/2004 | Foxlin |
| 6,759,200 B1 | 7/2004 | Stanton, Jr. |
| 6,847,336 B1 | 1/2005 | Lemelson et al. |
| 6,856,324 B2 | 2/2005 | Sauer et al. |
| 6,856,826 B2 | 2/2005 | Seeley et al. |
| 6,891,518 B2 | 5/2005 | Sauer et al. |
| 6,900,777 B1 | 5/2005 | Hebert et al. |
| 6,919,867 B2 | 7/2005 | Sauer |
| 6,921,167 B2 | 7/2005 | Nagata |
| 6,966,668 B2 | 11/2005 | Cugini et al. |
| 6,980,849 B2 | 12/2005 | Sasso |
| 6,993,374 B2 | 1/2006 | Sasso |
| 6,997,552 B1 | 2/2006 | Hung |
| 6,999,239 B1 | 2/2006 | Martins et al. |
| 7,000,262 B2 | 2/2006 | Bielefeld |
| 7,035,371 B2 | 4/2006 | Boese et al. |
| 7,043,961 B2 | 5/2006 | Pandey et al. |
| 7,072,435 B2 | 7/2006 | Metz et al. |
| 7,103,233 B2 | 9/2006 | Stearns |
| 7,107,091 B2 | 9/2006 | Jutras et al. |
| 7,112,656 B2 | 9/2006 | Desnoyers et al. |
| 7,141,812 B2 | 11/2006 | Appleby et al. |
| 7,157,459 B2 | 1/2007 | Ohta et al. |
| 7,169,785 B2 | 1/2007 | Timmer et al. |
| 7,171,255 B2 | 1/2007 | Holupka et al. |
| 7,176,936 B2 | 2/2007 | Sauer et al. |
| 7,187,792 B2 | 3/2007 | Fu et al. |
| 7,190,331 B2 | 3/2007 | Genc et al. |
| 7,194,295 B2 | 3/2007 | Stefan |
| 7,215,322 B2 | 5/2007 | Genc et al. |
| 7,229,078 B2 | 6/2007 | Lechot |
| 7,231,076 B2 | 6/2007 | Fu et al. |
| 7,235,076 B2 | 6/2007 | Pacheco |
| 7,239,330 B2 | 7/2007 | Sauer et al. |
| 7,241,292 B2 | 7/2007 | Hooven |
| 7,259,266 B2 | 8/2007 | Carter et al. |
| 7,260,426 B2 | 8/2007 | Schweikard et al. |
| 7,269,192 B2 | 9/2007 | Hayashi |
| 7,281,826 B2 | 10/2007 | Huang |
| 7,315,636 B2 | 1/2008 | Kuduvalli |
| 7,320,556 B2 | 1/2008 | Vagn-Erik |
| 7,330,578 B2 | 2/2008 | Wang et al. |
| 7,359,535 B2 | 4/2008 | Salla et al. |
| 7,364,314 B2 | 4/2008 | Nilsen et al. |
| 7,366,934 B1 | 4/2008 | Narayan et al. |
| 7,379,077 B2 | 5/2008 | Bani-Hashemi et al. |
| 7,431,453 B2 | 10/2008 | Hogan |
| 7,435,219 B2 | 10/2008 | Kim |
| 7,450,743 B2 | 11/2008 | Sundar et al. |
| 7,458,977 B2 | 12/2008 | McGinley et al. |
| 7,462,852 B2 | 12/2008 | Appleby et al. |
| 7,493,153 B2 | 2/2009 | Ahmed et al. |
| 7,505,617 B2 | 3/2009 | Fu et al. |
| 7,507,968 B2 | 3/2009 | Wollenweber et al. |
| 7,518,136 B2 | 4/2009 | Appleby et al. |
| 7,525,735 B2 | 4/2009 | Sottilare et al. |
| D592,691 S | 5/2009 | Chang |
| D592,692 S | 5/2009 | Chang |
| D592,693 S | 5/2009 | Chang |
| 7,536,216 B2 | 5/2009 | Geiger et al. |
| 7,542,791 B2 | 6/2009 | Mire et al. |
| 7,556,428 B2 | 7/2009 | Sukovic et al. |
| 7,557,824 B2 | 7/2009 | Holliman |
| 7,563,228 B2 | 7/2009 | Ma et al. |
| 7,567,834 B2 | 7/2009 | Clayton et al. |
| 7,570,791 B2 | 8/2009 | Frank et al. |
| 7,586,686 B1 | 9/2009 | Hall |
| D602,620 S | 10/2009 | Cristoforo |
| 7,605,826 B2 | 10/2009 | Sauer |
| 7,606,613 B2 | 10/2009 | Simon et al. |
| 7,607,775 B2 | 10/2009 | Hermanson et al. |
| 7,620,223 B2 | 11/2009 | Xu et al. |
| 7,623,902 B2 | 11/2009 | Pacheco |
| 7,627,085 B2 | 12/2009 | Boyden et al. |
| 7,630,753 B2 | 12/2009 | Simon et al. |
| 7,633,501 B2 | 12/2009 | Wood et al. |
| 7,645,050 B2 | 1/2010 | Wilt et al. |
| 7,653,226 B2 | 1/2010 | Guhring et al. |
| 7,657,075 B2 | 2/2010 | Viswanathan |
| 7,689,019 B2 | 3/2010 | Boese et al. |
| 7,689,042 B2 | 3/2010 | Brunner et al. |
| 7,689,320 B2 | 3/2010 | Prisco et al. |
| 7,699,486 B1 | 4/2010 | Beiner |
| 7,699,793 B2 | 4/2010 | Goette et al. |
| 7,719,769 B2 | 5/2010 | Sugihara et al. |

(56) References Cited

U.S. PATENT DOCUMENTS

| | | |
|---|---|---|
| D617,825 S | 6/2010 | Chang |
| 7,734,327 B2 | 6/2010 | Colquhoun |
| D619,285 S | 7/2010 | Cristoforo |
| 7,751,865 B2 | 7/2010 | Jascob et al. |
| 7,758,204 B2 | 7/2010 | Klipstein et al. |
| 7,768,702 B2 | 8/2010 | Hirose et al. |
| 7,769,236 B2 | 8/2010 | Fiala |
| 7,773,074 B2 | 8/2010 | Arenson et al. |
| 7,774,044 B2 | 8/2010 | Sauer et al. |
| 7,822,483 B2 | 10/2010 | Stone et al. |
| D628,307 S | 11/2010 | Krause-Bonte |
| 7,826,902 B2 | 11/2010 | Stone et al. |
| 7,831,073 B2 | 11/2010 | Fu et al. |
| 7,831,096 B2 | 11/2010 | Williamson, Jr. |
| 7,835,778 B2 | 11/2010 | Foley et al. |
| 7,835,784 B2 | 11/2010 | Mire et al. |
| 7,837,987 B2 | 11/2010 | Shi et al. |
| 7,840,093 B2 | 11/2010 | Fu et al. |
| 7,840,253 B2 | 11/2010 | Tremblay et al. |
| 7,840,256 B2 | 11/2010 | Lakin et al. |
| 7,853,305 B2 | 12/2010 | Simon et al. |
| 7,854,705 B2 | 12/2010 | Pawluczyk et al. |
| 7,857,271 B2 | 12/2010 | Lees |
| 7,860,282 B2 | 12/2010 | Boese et al. |
| D630,766 S | 1/2011 | Harbin |
| 7,865,269 B2 | 1/2011 | Prisco et al. |
| 7,874,686 B2 | 1/2011 | Rossner et al. |
| 7,881,770 B2 | 2/2011 | Melkent et al. |
| 7,893,413 B1 | 2/2011 | Appleby et al. |
| 7,894,649 B2 | 2/2011 | Fu et al. |
| 7,920,162 B2 | 4/2011 | Masini et al. |
| 7,922,391 B2 | 4/2011 | Essenreiter et al. |
| 7,938,553 B1 | 5/2011 | Beiner |
| 7,945,310 B2 | 5/2011 | Gattani et al. |
| 7,953,471 B2 | 5/2011 | Clayton et al. |
| 7,969,383 B2 | 6/2011 | Eberl et al. |
| 7,974,677 B2 | 7/2011 | Mire et al. |
| 7,985,756 B2 | 7/2011 | Barlow et al. |
| 7,991,557 B2 | 8/2011 | Liew et al. |
| 7,993,353 B2 | 8/2011 | Roner et al. |
| 7,996,064 B2 | 8/2011 | Simon et al. |
| 8,004,524 B2 | 8/2011 | Deinzer |
| 8,021,300 B2 | 9/2011 | Ma et al. |
| 8,022,984 B2 | 9/2011 | Cheong et al. |
| 8,045,266 B2 | 10/2011 | Nakamura |
| 8,060,181 B2 | 11/2011 | Rodriguez et al. |
| 8,068,581 B2 | 11/2011 | Boese et al. |
| 8,068,896 B2 | 11/2011 | Daghighian et al. |
| 8,077,943 B2 | 12/2011 | Williams et al. |
| 8,079,957 B2 | 12/2011 | Ma et al. |
| 8,081,812 B2 | 12/2011 | Kreiser |
| 8,085,075 B2 | 12/2011 | Huffman et al. |
| 8,085,897 B2 | 12/2011 | Morton |
| 8,090,175 B2 | 1/2012 | Fu et al. |
| 8,092,400 B2 | 1/2012 | Warkentine et al. |
| 8,108,072 B2 | 1/2012 | Zhao et al. |
| 8,112,292 B2 | 2/2012 | Simon |
| 8,116,847 B2 | 2/2012 | Gattani et al. |
| 8,120,847 B2 | 2/2012 | Chang |
| 8,121,255 B2 | 2/2012 | Sugiyama |
| 8,155,479 B2 | 4/2012 | Hoffman et al. |
| 8,180,132 B2 | 5/2012 | Gorges et al. |
| 8,180,429 B2 | 5/2012 | Sasso |
| 8,208,599 B2 | 6/2012 | Ye et al. |
| 8,216,211 B2 | 7/2012 | Mathis et al. |
| 8,221,402 B2 | 7/2012 | Francischelli et al. |
| 8,239,001 B2 | 8/2012 | Verard et al. |
| 8,244,012 B2 | 8/2012 | Liang et al. |
| 8,253,778 B2 | 8/2012 | Atsushi |
| 8,271,069 B2 | 9/2012 | Jascob et al. |
| 8,280,491 B2 | 10/2012 | Kuduvalli et al. |
| 8,285,021 B2 | 10/2012 | Boese et al. |
| 8,300,315 B2 | 10/2012 | Kobayashi |
| 8,305,685 B2 | 11/2012 | Heine et al. |
| 8,306,305 B2 | 11/2012 | Porat et al. |
| 8,309,932 B2 | 11/2012 | Haselman et al. |
| 8,317,320 B2 | 11/2012 | Huang |
| 8,328,815 B2 | 12/2012 | Farr et al. |
| 8,335,553 B2 | 12/2012 | Rubner et al. |
| 8,335,557 B2 | 12/2012 | Maschke |
| 8,340,379 B2 | 12/2012 | Razzaque et al. |
| 8,369,925 B2 | 2/2013 | Giesel et al. |
| 8,386,022 B2 | 2/2013 | Jutras et al. |
| 8,394,144 B2 | 3/2013 | Zehavi et al. |
| 8,398,541 B2 | 3/2013 | DiMaio et al. |
| 8,444,266 B2 | 5/2013 | Waters |
| 8,457,719 B2 | 6/2013 | Moctezuma De La Barrera et al. |
| 8,467,851 B2 | 6/2013 | Mire et al. |
| 8,469,902 B2 | 6/2013 | Dick et al. |
| 8,475,470 B2 | 7/2013 | Von Jako |
| 8,494,612 B2 | 7/2013 | Vetter et al. |
| 8,509,503 B2 | 8/2013 | Nahum et al. |
| 8,511,827 B2 | 8/2013 | Hua et al. |
| 8,531,394 B2 | 9/2013 | Maltz |
| 8,540,364 B2 | 9/2013 | Waters |
| 8,545,012 B2 | 10/2013 | Waters |
| 8,548,567 B2 | 10/2013 | Maschke et al. |
| 8,556,883 B2 | 10/2013 | Saleh |
| 8,559,596 B2 | 10/2013 | Thomson et al. |
| 8,567,945 B2 | 10/2013 | Waters |
| 8,571,353 B2 | 10/2013 | Watanabe |
| 8,585,598 B2 | 11/2013 | Razzaque et al. |
| 8,600,001 B2 | 12/2013 | Schweizer |
| 8,600,477 B2 | 12/2013 | Beyar et al. |
| 8,605,199 B2 | 12/2013 | Imai |
| 8,611,988 B2 | 12/2013 | Miyamoto |
| 8,612,024 B2 | 12/2013 | Stone et al. |
| 8,634,897 B2 | 1/2014 | Simon et al. |
| 8,641,621 B2 | 2/2014 | Razzaque et al. |
| 8,643,950 B2 | 2/2014 | König |
| 8,644,907 B2 | 2/2014 | Hartmann et al. |
| 8,674,902 B2 | 3/2014 | Park et al. |
| 8,686,923 B2 | 4/2014 | Eberl et al. |
| 8,690,581 B2 | 4/2014 | Ruf et al. |
| 8,690,776 B2 | 4/2014 | Razzaque et al. |
| 8,692,845 B2 | 4/2014 | Fedorovskaya et al. |
| 8,693,632 B2 | 4/2014 | Allison |
| 8,694,075 B2 | 4/2014 | Groszmann et al. |
| 8,699,765 B2 | 4/2014 | Hao et al. |
| 8,705,829 B2 | 4/2014 | Frank et al. |
| 8,737,708 B2 | 5/2014 | Hartmann et al. |
| 8,746,887 B2 | 6/2014 | Shestak et al. |
| 8,764,025 B1 | 7/2014 | Gao |
| 8,784,450 B2 | 7/2014 | Moskowitz et al. |
| 8,786,689 B1 | 7/2014 | Liu |
| D710,545 S | 8/2014 | Wu |
| D710,546 S | 8/2014 | Wu |
| 8,827,934 B2 | 9/2014 | Chopra et al. |
| 8,831,706 B2 | 9/2014 | Fu et al. |
| 8,836,768 B1 | 9/2014 | Rafii et al. |
| 8,838,199 B2 | 9/2014 | Simon et al. |
| 8,848,977 B2 | 9/2014 | Bammer et al. |
| 8,855,395 B2 | 10/2014 | Baturin et al. |
| 8,878,900 B2 | 11/2014 | Yang et al. |
| 8,879,815 B2 | 11/2014 | Miao et al. |
| 8,885,177 B2 | 11/2014 | Ben-Yishai et al. |
| 8,890,772 B2 | 11/2014 | Woo et al. |
| 8,890,773 B1 | 11/2014 | Pederson |
| 8,890,943 B2 | 11/2014 | Lee et al. |
| 8,897,514 B2 | 11/2014 | Feikas et al. |
| 8,900,131 B2 | 12/2014 | Chopra et al. |
| 8,903,150 B2 | 12/2014 | Star-Lack et al. |
| 8,908,952 B2 | 12/2014 | Isaacs et al. |
| 8,911,358 B2 | 12/2014 | Koninckx et al. |
| 8,917,268 B2 | 12/2014 | Johnsen et al. |
| 8,920,776 B2 | 12/2014 | Gaiger et al. |
| 8,922,589 B2 | 12/2014 | Laor |
| 8,941,559 B2 | 1/2015 | Bar-Zeev et al. |
| 8,942,455 B2 | 1/2015 | Chou et al. |
| 8,950,877 B2 | 2/2015 | Northey et al. |
| 8,953,246 B2 | 2/2015 | Koenig |
| 8,965,583 B2 | 2/2015 | Ortmaier et al. |
| 8,969,829 B2 | 3/2015 | Wollenweber et al. |
| 8,989,349 B2 | 3/2015 | Thomson et al. |

(56) References Cited

U.S. PATENT DOCUMENTS

| | | |
|---|---|---|
| 8,992,580 B2 | 3/2015 | Bar et al. |
| 8,994,729 B2 | 3/2015 | Nakamura |
| 8,994,795 B2 | 3/2015 | Oh |
| 9,004,711 B2 | 4/2015 | Gerolemou |
| 9,005,211 B2 | 4/2015 | Brundobler et al. |
| 9,011,441 B2 | 4/2015 | Bertagnoli et al. |
| 9,057,759 B2 | 6/2015 | Klingenbeck et al. |
| 9,060,757 B2 | 6/2015 | Lawson et al. |
| 9,066,751 B2 | 6/2015 | Sasso |
| 9,081,436 B1 | 7/2015 | Berme et al. |
| 9,084,635 B2 | 7/2015 | Nuckley et al. |
| 9,085,643 B2 | 7/2015 | Svanborg et al. |
| 9,087,471 B2 | 7/2015 | Miao |
| 9,100,643 B2 | 8/2015 | McDowall et al. |
| 9,101,394 B2 | 8/2015 | Arata et al. |
| 9,104,902 B2 | 8/2015 | Xu et al. |
| 9,111,175 B2 | 8/2015 | Strommer et al. |
| 9,123,155 B2 | 9/2015 | Cunningham et al. |
| 9,125,556 B2 | 9/2015 | Zehavi et al. |
| 9,129,054 B2 | 9/2015 | Nawana et al. |
| 9,129,372 B2 | 9/2015 | Kriston et al. |
| 9,132,361 B2 | 9/2015 | Smithwick |
| 9,135,706 B2 | 9/2015 | Zagorchev et al. |
| 9,141,873 B2 | 9/2015 | Takemoto |
| 9,142,020 B2 | 9/2015 | Deguise et al. |
| 9,149,317 B2 | 10/2015 | Arthur et al. |
| 9,165,203 B2 | 10/2015 | McCarthy |
| 9,165,362 B2 | 10/2015 | Siewerdsen et al. |
| 9,179,984 B2 | 11/2015 | Teichman et al. |
| D746,354 S | 12/2015 | Chang |
| 9,208,916 B2 | 12/2015 | Appleby et al. |
| 9,220,573 B2 | 12/2015 | Kendrick et al. |
| 9,225,895 B2 | 12/2015 | Kozinski |
| 9,232,982 B2 | 1/2016 | Soler et al. |
| 9,235,934 B2 | 1/2016 | Mandella et al. |
| 9,240,046 B2 | 1/2016 | Carrell et al. |
| 9,244,278 B2 | 1/2016 | Sugiyama et al. |
| 9,247,240 B2 | 1/2016 | Park et al. |
| 9,259,192 B2 | 2/2016 | Ishihara |
| 9,265,572 B2 | 2/2016 | Fuchs et al. |
| 9,269,192 B2 | 2/2016 | Kobayashi |
| 9,283,052 B2 | 3/2016 | Rodriguez Ponce |
| 9,286,730 B2 | 3/2016 | Bar-Zeev et al. |
| 9,289,267 B2 | 3/2016 | Sauer et al. |
| 9,294,222 B2 | 3/2016 | Proctor, Jr. |
| 9,300,949 B2 | 3/2016 | Ahearn |
| 9,305,354 B2 | 4/2016 | Burlon et al. |
| 9,310,591 B2 | 4/2016 | Hua et al. |
| 9,320,474 B2 | 4/2016 | Demri et al. |
| 9,323,055 B2 | 4/2016 | Baillot |
| 9,330,477 B2 | 5/2016 | Rappel |
| 9,335,547 B2 | 5/2016 | Takano et al. |
| 9,335,567 B2 | 5/2016 | Nakamura |
| 9,341,704 B2 | 5/2016 | Picard et al. |
| 9,344,686 B2 | 5/2016 | Moharir |
| 9,349,066 B2 | 5/2016 | Koo et al. |
| 9,349,520 B2 | 5/2016 | Demetriou et al. |
| 9,364,294 B2 | 6/2016 | Razzaque et al. |
| 9,370,332 B2 | 6/2016 | Paladini et al. |
| 9,373,166 B2 | 6/2016 | Azar |
| 9,375,639 B2 | 6/2016 | Kobayashi et al. |
| 9,378,558 B2 | 6/2016 | Kajiwara et al. |
| 9,380,287 B2 | 6/2016 | Nistico et al. |
| 9,387,008 B2 | 7/2016 | Sarvestani et al. |
| 9,392,129 B2 | 7/2016 | Simmons |
| 9,395,542 B2 | 7/2016 | Tilleman et al. |
| 9,398,936 B2 | 7/2016 | Razzaque et al. |
| 9,400,384 B2 | 7/2016 | Griffith |
| 9,414,041 B2 | 8/2016 | Ko et al. |
| 9,424,611 B2 | 8/2016 | Kanjirathinkal et al. |
| 9,424,641 B2 | 8/2016 | Wiemker et al. |
| 9,427,286 B2 | 8/2016 | Siewerdsen et al. |
| 9,438,894 B2 | 9/2016 | Park et al. |
| 9,443,488 B2 | 9/2016 | Borenstein et al. |
| 9,453,804 B2 | 9/2016 | Tahtali |
| 9,456,878 B2 | 10/2016 | MacFarlane et al. |
| 9,465,235 B2 | 10/2016 | Chang |
| 9,468,373 B2 | 10/2016 | Larsen |
| 9,470,908 B1 | 10/2016 | Frankel et al. |
| 9,473,766 B2 | 10/2016 | Douglas et al. |
| 9,492,222 B2 | 11/2016 | Singh |
| 9,495,585 B2 | 11/2016 | Bicer et al. |
| 9,498,132 B2 | 11/2016 | Maier-Hein et al. |
| 9,498,231 B2 | 11/2016 | Haider et al. |
| 9,499,999 B2 | 11/2016 | Zhou |
| 9,507,155 B2 | 11/2016 | Morimoto |
| 9,513,495 B2 | 12/2016 | Waters |
| 9,521,966 B2 | 12/2016 | Schwartz |
| 9,526,443 B1 | 12/2016 | Berme et al. |
| 9,530,382 B2 | 12/2016 | Simmons |
| 9,532,846 B2 | 1/2017 | Nakamura |
| 9,532,849 B2 | 1/2017 | Anderson et al. |
| 9,533,407 B1 | 1/2017 | Ragner |
| 9,538,962 B1 | 1/2017 | Hannaford et al. |
| 9,545,233 B2 | 1/2017 | Sirpad et al. |
| 9,546,779 B2 | 1/2017 | Rementer |
| 9,547,174 B2 | 1/2017 | Gao et al. |
| 9,547,940 B1 | 1/2017 | Sun et al. |
| 9,557,566 B2 | 1/2017 | Fujimaki |
| 9,560,318 B2 | 1/2017 | Reina et al. |
| 9,561,095 B1 | 2/2017 | Nguyen et al. |
| 9,561,446 B2 | 2/2017 | Brecher |
| 9,565,415 B2 | 2/2017 | Zhang et al. |
| 9,572,661 B2 | 2/2017 | Robin et al. |
| 9,576,398 B1 | 2/2017 | Zehner et al. |
| 9,576,556 B2 | 2/2017 | Simmons |
| 9,581,822 B2 | 2/2017 | Morimoto |
| 9,610,056 B2 | 4/2017 | Lavallee et al. |
| 9,612,657 B2 | 4/2017 | Bertram et al. |
| 9,626,936 B2 | 4/2017 | Bell |
| 9,629,595 B2 | 4/2017 | Walker et al. |
| 9,633,431 B2 | 4/2017 | Merlet |
| 9,645,395 B2 | 5/2017 | Bolas et al. |
| 9,646,423 B1 | 5/2017 | Sun et al. |
| 9,672,597 B2 | 6/2017 | Amiot et al. |
| 9,672,607 B2 | 6/2017 | Demri et al. |
| 9,672,640 B2 | 6/2017 | Kleiner |
| 9,675,306 B2 | 6/2017 | Morton |
| 9,675,319 B1 | 6/2017 | Razzaque et al. |
| 9,684,980 B2 | 6/2017 | Royalty et al. |
| 9,690,119 B2 | 6/2017 | Garofolo et al. |
| RE46,463 E | 7/2017 | Fienbloom et al. |
| 9,693,748 B2 | 7/2017 | Rai et al. |
| 9,710,968 B2 | 7/2017 | Dillavou et al. |
| 9,713,502 B2 | 7/2017 | Finkman et al. |
| 9,724,119 B2 | 8/2017 | Hissong et al. |
| 9,724,165 B2 | 8/2017 | Arata et al. |
| 9,726,888 B2 | 8/2017 | Giartosio et al. |
| 9,728,006 B2 | 8/2017 | Varga |
| 9,729,831 B2 | 8/2017 | Birnkrant et al. |
| 9,746,739 B2 | 8/2017 | Alton et al. |
| 9,757,034 B2 | 9/2017 | Desjardins et al. |
| 9,757,087 B2 | 9/2017 | Simon et al. |
| 9,766,441 B2 | 9/2017 | Rappel |
| 9,766,459 B2 | 9/2017 | Alton et al. |
| 9,767,608 B2 | 9/2017 | Lee et al. |
| 9,770,203 B1 | 9/2017 | Berme et al. |
| 9,772,102 B1 | 9/2017 | Ferguson |
| 9,772,495 B2 | 9/2017 | Tam et al. |
| 9,791,138 B1 | 10/2017 | Feinbloom et al. |
| 9,800,995 B2 | 10/2017 | Libin et al. |
| 9,805,504 B2 | 10/2017 | Zhang et al. |
| 9,808,148 B2 | 11/2017 | Miller et al. |
| 9,839,448 B2 | 12/2017 | Reckling et al. |
| 9,844,413 B2 | 12/2017 | Daon et al. |
| 9,851,080 B2 | 12/2017 | Wilt et al. |
| 9,858,663 B2 | 1/2018 | Penney et al. |
| 9,861,446 B2 | 1/2018 | Lang |
| 9,864,214 B2 | 1/2018 | Fass |
| 9,872,733 B2 | 1/2018 | Shoham et al. |
| 9,875,544 B2 | 1/2018 | Rai et al. |
| 9,877,642 B2 | 1/2018 | Duret |
| 9,885,465 B2 | 2/2018 | Nguyen |
| 9,886,552 B2 | 2/2018 | Dillavou et al. |

(56) References Cited

U.S. PATENT DOCUMENTS

| | | |
|---|---|---|
| 9,886,760 B2 | 2/2018 | Liu et al. |
| 9,892,564 B1 | 2/2018 | Cvetko et al. |
| 9,898,866 B2 | 2/2018 | Fuchs et al. |
| 9,901,414 B2 | 2/2018 | Lively et al. |
| 9,911,187 B2 | 3/2018 | Steinle et al. |
| 9,911,236 B2 | 3/2018 | Bar et al. |
| 9,927,611 B2 | 3/2018 | Rudy et al. |
| 9,928,629 B2 | 3/2018 | Benishti et al. |
| 9,940,750 B2 | 4/2018 | Dillavou et al. |
| 9,943,374 B2 | 4/2018 | Merritt et al. |
| 9,947,110 B2 | 4/2018 | Haimerl |
| 9,952,664 B2 | 4/2018 | Border et al. |
| 9,956,054 B2 | 5/2018 | Aguirre-Valencia |
| 9,958,674 B2 | 5/2018 | Border |
| 9,959,620 B2 | 5/2018 | Merlet |
| 9,959,629 B2 | 5/2018 | Dillavou et al. |
| 9,965,681 B2 | 5/2018 | Border et al. |
| 9,968,297 B2 | 5/2018 | Connor |
| 9,980,780 B2 | 5/2018 | Lang |
| 9,986,228 B2 | 5/2018 | Woods |
| D824,523 S | 7/2018 | Paoli et al. |
| 10,010,379 B1 | 7/2018 | Gibby et al. |
| 10,013,531 B2 | 7/2018 | Richards et al. |
| 10,015,243 B2 | 7/2018 | Kazerani et al. |
| 10,016,243 B2 | 7/2018 | Esterberg |
| 10,022,064 B2 | 7/2018 | Kim et al. |
| 10,022,065 B2 | 7/2018 | Ben-Yishai et al. |
| 10,022,104 B2 | 7/2018 | Sell et al. |
| 10,023,615 B2 | 7/2018 | Bonny |
| 10,026,015 B2 | 7/2018 | Cavusoglu et al. |
| 10,034,713 B2 | 7/2018 | Yang et al. |
| 10,042,167 B2 | 8/2018 | McDowall et al. |
| 10,046,165 B2 | 8/2018 | Frewin et al. |
| 10,055,838 B2 | 8/2018 | Elenbaas et al. |
| 10,066,816 B2 | 9/2018 | Chang |
| 10,067,359 B1 | 9/2018 | Ushakov |
| 10,073,515 B2 | 9/2018 | Awdeh |
| 10,080,616 B2 | 9/2018 | Wilkinson et al. |
| 10,082,680 B2 | 9/2018 | Chung |
| 10,085,709 B2 | 10/2018 | Lavallee et al. |
| 10,105,187 B2 | 10/2018 | Corndorf et al. |
| 10,107,483 B2 | 10/2018 | Oren |
| 10,108,833 B2 | 10/2018 | Hong et al. |
| 10,123,840 B2 | 11/2018 | Dorman |
| 10,130,378 B2 | 11/2018 | Bryan |
| 10,132,483 B1 | 11/2018 | Feinbloom et al. |
| 10,134,166 B2 | 11/2018 | Benishti et al. |
| 10,134,194 B2 | 11/2018 | Kepner et al. |
| 10,139,652 B2 | 11/2018 | Windham |
| 10,139,920 B2 | 11/2018 | Isaacs et al. |
| 10,142,496 B1 | 11/2018 | Rao et al. |
| 10,151,928 B2 | 12/2018 | Ushakov |
| 10,154,239 B2 | 12/2018 | Casas |
| 10,159,530 B2 | 12/2018 | Lang |
| 10,163,207 B2 | 12/2018 | Merlet |
| 10,166,079 B2 | 1/2019 | McLachlin et al. |
| 10,175,507 B2 | 1/2019 | Nakamura |
| 10,175,753 B2 | 1/2019 | Boesen |
| 10,181,361 B2 | 1/2019 | Dillavou et al. |
| 10,186,055 B2 | 1/2019 | Takahashi et al. |
| 10,188,672 B2 | 1/2019 | Wagner |
| 10,194,131 B2 | 1/2019 | Casas |
| 10,194,990 B2 | 2/2019 | Amanatullah et al. |
| 10,194,993 B2 | 2/2019 | Roger et al. |
| 10,195,076 B2 | 2/2019 | Fateh |
| 10,197,803 B2 | 2/2019 | Badiali et al. |
| 10,197,816 B2 | 2/2019 | Waisman et al. |
| 10,207,315 B2 | 2/2019 | Appleby et al. |
| 10,212,517 B1 | 2/2019 | Beltran et al. |
| 10,230,719 B2 | 3/2019 | Vaughn et al. |
| 10,231,893 B2 | 3/2019 | Lei et al. |
| 10,235,606 B2 | 3/2019 | Miao et al. |
| 10,240,769 B1 | 3/2019 | Braganca et al. |
| 10,247,965 B2 | 4/2019 | Ton |
| 10,251,724 B2 | 4/2019 | McLachlin et al. |
| 10,261,324 B2 | 4/2019 | Chuang et al. |
| 10,262,424 B2 | 4/2019 | Ketcha et al. |
| 10,274,731 B2 | 4/2019 | Maimone |
| 10,278,777 B1 | 5/2019 | Lang |
| 10,292,768 B2 | 5/2019 | Lang |
| 10,296,805 B2 | 5/2019 | Yang et al. |
| 10,319,154 B1 | 6/2019 | Chakravarthula et al. |
| 10,326,975 B2 | 6/2019 | Casas |
| 10,332,267 B2 | 6/2019 | Rai et al. |
| 10,339,719 B2 | 7/2019 | Jagga et al. |
| 10,352,543 B1 | 7/2019 | Braganca et al. |
| 10,357,146 B2 | 7/2019 | Fiebel et al. |
| 10,357,574 B2 | 7/2019 | Hilderbrand et al. |
| 10,366,489 B2 | 7/2019 | Boettger et al. |
| 10,368,947 B2 | 8/2019 | Lang |
| 10,368,948 B2 | 8/2019 | Tripathi |
| 10,382,748 B2 | 8/2019 | Benishti et al. |
| 10,383,654 B2 | 8/2019 | Yilmaz et al. |
| 10,386,645 B2 | 8/2019 | Abou Shousha |
| 10,388,076 B2 | 8/2019 | Bar-Zeev et al. |
| 10,398,514 B2 | 9/2019 | Ryan et al. |
| 10,401,657 B2 | 9/2019 | Jiang et al. |
| 10,405,825 B2 | 9/2019 | Rai et al. |
| 10,405,927 B1 | 9/2019 | Lang |
| 10,413,752 B2 | 9/2019 | Berlinger et al. |
| 10,419,655 B2 | 9/2019 | Sivan |
| 10,420,626 B2 | 9/2019 | Tokuda et al. |
| 10,420,813 B2 | 9/2019 | Newell-Rogers et al. |
| 10,424,115 B2 | 9/2019 | Ellerbrock |
| D862,469 S | 10/2019 | Sadot et al. |
| 10,426,554 B2 | 10/2019 | Siewerdsen et al. |
| 10,429,675 B2 | 10/2019 | Greget |
| 10,431,008 B2 | 10/2019 | Djajadiningrat et al. |
| 10,433,814 B2 | 10/2019 | Razzaque et al. |
| 10,434,335 B2 | 10/2019 | Takahashi et al. |
| 10,441,236 B2 | 10/2019 | Bar-Tal et al. |
| 10,444,514 B2 | 10/2019 | Abou Shousha et al. |
| 10,447,947 B2 | 10/2019 | Liu |
| 10,448,003 B2 | 10/2019 | Grafenberg |
| 10,449,040 B2 | 10/2019 | Lashinski et al. |
| 10,453,187 B2 | 10/2019 | Peterson et al. |
| 10,463,434 B2 | 11/2019 | Siegler et al. |
| 10,465,892 B1 | 11/2019 | Feinbloom et al. |
| 10,466,487 B2 | 11/2019 | Blum et al. |
| 10,470,732 B2 | 11/2019 | Baumgart et al. |
| 10,473,314 B1 | 11/2019 | Braganca et al. |
| 10,485,989 B2 | 11/2019 | Jordan et al. |
| 10,488,663 B2 | 11/2019 | Choi |
| D869,772 S | 12/2019 | Gand |
| D870,977 S | 12/2019 | Berggren et al. |
| 10,492,755 B2 | 12/2019 | Lin et al. |
| 10,499,997 B2 | 12/2019 | Weinstein et al. |
| 10,502,363 B2 | 12/2019 | Edwards et al. |
| 10,504,231 B2 | 12/2019 | Fiala |
| 10,507,066 B2 | 12/2019 | DiMaio et al. |
| 10,511,822 B2 | 12/2019 | Casas |
| 10,517,544 B2 | 12/2019 | Taguchi et al. |
| 10,537,395 B2 | 1/2020 | Perez |
| 10,540,780 B1 | 1/2020 | Cousins et al. |
| 10,543,485 B2 | 1/2020 | Ismagilov et al. |
| 10,546,423 B2 | 1/2020 | Jones et al. |
| 10,548,557 B2 | 2/2020 | Lim et al. |
| 10,555,775 B2 | 2/2020 | Hoffman et al. |
| 10,568,535 B2 | 2/2020 | Roberts et al. |
| 10,571,696 B2 | 2/2020 | Urey et al. |
| 10,571,716 B2 | 2/2020 | Chapiro |
| 10,573,086 B2 | 2/2020 | Bar-Zeev et al. |
| 10,573,087 B2 | 2/2020 | Gallop et al. |
| 10,577,630 B2 | 3/2020 | Zhang et al. |
| 10,586,400 B2 | 3/2020 | Douglas |
| 10,591,737 B2 | 3/2020 | Yildiz et al. |
| 10,592,748 B2 | 3/2020 | Cousins et al. |
| 10,594,998 B1 | 3/2020 | Casas |
| 10,595,716 B2 | 3/2020 | Nazareth et al. |
| 10,601,950 B2 | 3/2020 | Devam et al. |
| 10,602,114 B2 | 3/2020 | Casas |
| 10,603,113 B2 | 3/2020 | Lang |
| 10,603,133 B2 | 3/2020 | Wang et al. |
| 10,606,085 B2 | 3/2020 | Toyama |

(56) References Cited

U.S. PATENT DOCUMENTS

| | | |
|---|---|---|
| 10,610,172 B2 | 4/2020 | Hummel et al. |
| 10,610,179 B2 | 4/2020 | Altmann |
| 10,613,352 B2 | 4/2020 | Knoll |
| 10,617,566 B2 | 4/2020 | Esmonde |
| 10,620,460 B2 | 4/2020 | Carabin |
| 10,621,738 B2 | 4/2020 | Miao et al. |
| 10,625,099 B2 | 4/2020 | Takahashi et al. |
| 10,626,473 B2 | 4/2020 | Mariani et al. |
| 10,631,905 B2 | 4/2020 | Asfora et al. |
| 10,631,907 B2 | 4/2020 | Zucker et al. |
| 10,634,331 B1 | 4/2020 | Feinbloom et al. |
| 10,634,921 B2 | 4/2020 | Blum et al. |
| 10,638,080 B2 | 4/2020 | Ovchinnikov et al. |
| 10,646,285 B2 | 5/2020 | Siemionow et al. |
| 10,650,513 B2 | 5/2020 | Penney et al. |
| 10,650,594 B2 | 5/2020 | Jones et al. |
| 10,652,525 B2 | 5/2020 | Woods |
| 10,653,495 B2 | 5/2020 | Gregerson et al. |
| 10,660,715 B2 | 5/2020 | Dozeman |
| 10,663,738 B2 | 5/2020 | Carlvik et al. |
| 10,665,033 B2 | 5/2020 | Bar-Zeev et al. |
| 10,670,937 B2 | 6/2020 | Alton et al. |
| 10,672,145 B2 | 6/2020 | Albiol et al. |
| 10,682,112 B2 | 6/2020 | Pizaine et al. |
| 10,682,767 B2 | 6/2020 | Grafenberg et al. |
| 10,687,901 B2 | 6/2020 | Thomas |
| 10,691,397 B1 | 6/2020 | Clements |
| 10,702,713 B2 | 7/2020 | Mori et al. |
| 10,706,540 B2 | 7/2020 | Merlet |
| 10,709,398 B2 | 7/2020 | Schweizer |
| 10,713,801 B2 | 7/2020 | Jordan et al. |
| 10,716,643 B2 | 7/2020 | Justin et al. |
| 10,722,733 B2 | 7/2020 | Takahashi |
| 10,725,535 B2 | 7/2020 | Yu |
| 10,731,832 B2 | 8/2020 | Koo |
| 10,732,721 B1 | 8/2020 | Clements |
| 10,742,949 B2 | 8/2020 | Casas |
| 10,743,939 B1 | 8/2020 | Lang |
| 10,743,943 B2 | 8/2020 | Razeto et al. |
| 10,747,315 B2 | 8/2020 | Tungare et al. |
| 10,748,319 B1 | 8/2020 | Tao et al. |
| 10,758,315 B2 | 9/2020 | Johnson et al. |
| 10,777,094 B1 | 9/2020 | Rao et al. |
| 10,777,315 B2 | 9/2020 | Zehavi et al. |
| 10,781,482 B2 | 9/2020 | Gubatayao et al. |
| 10,792,110 B2 | 10/2020 | Leung et al. |
| 10,799,145 B2 | 10/2020 | West et al. |
| 10,799,296 B2 | 10/2020 | Lang |
| 10,799,298 B2 | 10/2020 | Crawford et al. |
| 10,799,316 B2 | 10/2020 | Sela et al. |
| 10,810,799 B2 | 10/2020 | Tepper et al. |
| 10,818,019 B2 | 10/2020 | Piat et al. |
| 10,818,101 B2 | 10/2020 | Gallop et al. |
| 10,818,199 B2 | 10/2020 | Buras et al. |
| 10,825,563 B2 | 11/2020 | Gibby et al. |
| 10,827,164 B2 | 11/2020 | Perreault et al. |
| 10,831,943 B2 | 11/2020 | Santarone et al. |
| 10,835,296 B2 | 11/2020 | Elimelech et al. |
| 10,838,206 B2 | 11/2020 | Fortin-Deschnes et al. |
| 10,839,629 B2 | 11/2020 | Jones et al. |
| 10,839,956 B2 | 11/2020 | Beydoun et al. |
| 10,841,556 B2 | 11/2020 | Casas |
| 10,842,002 B2 | 11/2020 | Chang |
| 10,842,461 B2 | 11/2020 | Johnson et al. |
| 10,849,691 B2 | 12/2020 | Zucker et al. |
| 10,849,693 B2 | 12/2020 | Lang |
| 10,849,710 B2 | 12/2020 | Liu |
| 10,861,236 B2 | 12/2020 | Geri et al. |
| 10,865,220 B2 | 12/2020 | Ebetino et al. |
| 10,869,517 B1 | 12/2020 | Halpern |
| 10,869,727 B2 | 12/2020 | Yanof et al. |
| 10,872,472 B2 | 12/2020 | Watola et al. |
| 10,877,262 B1 | 12/2020 | Luxembourg |
| 10,877,296 B2 | 12/2020 | Lindsey et al. |
| 10,878,639 B2 | 12/2020 | Douglas et al. |
| 10,893,260 B2 | 1/2021 | Trail et al. |
| 10,895,742 B2 | 1/2021 | Schneider et al. |
| 10,895,743 B2 | 1/2021 | Dausmann |
| 10,895,906 B2 | 1/2021 | West et al. |
| 10,898,151 B2 | 1/2021 | Harding et al. |
| 10,908,420 B2 | 2/2021 | Lee et al. |
| 10,921,595 B2 | 2/2021 | Rakshit et al. |
| 10,921,613 B2 | 2/2021 | Gupta et al. |
| 10,928,321 B2 | 2/2021 | Rawle |
| 10,928,638 B2 | 2/2021 | Ninan et al. |
| 10,929,670 B1 | 2/2021 | Troy et al. |
| 10,935,815 B1 | 3/2021 | Castaeda |
| 10,935,816 B2 | 3/2021 | Ban et al. |
| 10,936,537 B2 | 3/2021 | Huston |
| 10,939,973 B2 | 3/2021 | DiMaio et al. |
| 10,939,977 B2 | 3/2021 | Messinger et al. |
| 10,941,933 B2 | 3/2021 | Ferguson |
| 10,946,108 B2 | 3/2021 | Zhang et al. |
| 10,950,338 B2 | 3/2021 | Douglas |
| 10,951,872 B2 | 3/2021 | Casas |
| 10,964,095 B1 | 3/2021 | Douglas |
| 10,964,124 B1 | 3/2021 | Douglas |
| 10,966,768 B2 | 4/2021 | Poulos |
| 10,969,587 B2 | 4/2021 | McDowall et al. |
| 10,993,754 B2 | 5/2021 | Kuntz et al. |
| 11,000,335 B2 | 5/2021 | Dorman |
| 11,002,994 B2 | 5/2021 | Jiang et al. |
| 11,006,093 B1 | 5/2021 | Hegyi |
| 11,013,550 B2 | 5/2021 | Rioux et al. |
| 11,013,560 B2 | 5/2021 | Lang |
| 11,013,562 B2 | 5/2021 | Marti et al. |
| 11,013,573 B2 | 5/2021 | Chang |
| 11,013,900 B2 | 5/2021 | Malek et al. |
| 11,016,302 B2 | 5/2021 | Freeman et al. |
| 11,019,988 B2 | 6/2021 | Fiebel et al. |
| 11,027,027 B2 | 6/2021 | Manning et al. |
| 11,029,147 B2 | 6/2021 | Abovitz et al. |
| 11,030,809 B2 | 6/2021 | Wang |
| 11,041,173 B2 | 6/2021 | Zhang et al. |
| 11,045,663 B2 | 6/2021 | Mori et al. |
| 11,049,293 B2 | 6/2021 | Chae et al. |
| 11,049,476 B2 | 6/2021 | Fuchs et al. |
| 11,050,990 B2 | 6/2021 | Casas |
| 11,057,505 B2 | 7/2021 | Dharmatilleke |
| 11,058,390 B1 | 7/2021 | Douglas |
| 11,061,257 B1 | 7/2021 | Hakim |
| 11,064,904 B2 | 7/2021 | Kay et al. |
| 11,065,062 B2 | 7/2021 | Frushour et al. |
| 11,067,387 B2 | 7/2021 | Marell et al. |
| 11,071,497 B2 | 7/2021 | Hallack et al. |
| 11,079,596 B2 | 8/2021 | Hua et al. |
| 11,087,039 B2 | 8/2021 | Duff et al. |
| 11,090,019 B2 | 8/2021 | Siemionow et al. |
| 11,097,129 B2 | 8/2021 | Sakata et al. |
| 11,099,376 B1 | 8/2021 | Steier et al. |
| 11,103,320 B2 | 8/2021 | LeBoeuf et al. |
| D930,162 S | 9/2021 | Cremer et al. |
| 11,109,762 B1 | 9/2021 | Steier et al. |
| 11,112,611 B1 | 9/2021 | Kessler et al. |
| 11,122,164 B2 | 9/2021 | Gigante |
| 11,123,604 B2 | 9/2021 | Fung |
| 11,129,562 B2 | 9/2021 | Roberts et al. |
| 11,132,055 B2 | 9/2021 | Jones et al. |
| 11,135,015 B2 | 10/2021 | Crawford et al. |
| 11,135,016 B2 | 10/2021 | Frielinghaus et al. |
| 11,137,610 B1 | 10/2021 | Kessler et al. |
| 11,141,221 B2 | 10/2021 | Hobeika et al. |
| 11,153,549 B2 | 10/2021 | Casas |
| 11,153,555 B1 | 10/2021 | Healy et al. |
| 11,163,176 B2 | 11/2021 | Karafin et al. |
| 11,164,324 B2 | 11/2021 | Liu et al. |
| 11,166,006 B2 | 11/2021 | Hegyi |
| 11,169,380 B2 | 11/2021 | Manly et al. |
| 11,172,990 B2 | 11/2021 | Lang |
| 11,179,136 B2 | 11/2021 | Kohli et al. |
| 11,180,557 B2 | 11/2021 | Noelle |
| 11,181,747 B1 | 11/2021 | Kessler et al. |
| 11,185,891 B2 | 11/2021 | Cousins et al. |
| 11,187,907 B2 | 11/2021 | Osterman et al. |

(56) References Cited

U.S. PATENT DOCUMENTS

| | | |
|---|---|---|
| 11,202,682 B2 | 12/2021 | Staunton et al. |
| 11,207,150 B2 | 12/2021 | Healy et al. |
| 11,217,028 B2 | 1/2022 | Jones et al. |
| 11,224,483 B2 | 1/2022 | Steinberg et al. |
| 11,224,763 B2 | 1/2022 | Takahashi et al. |
| 11,227,417 B2 | 1/2022 | Berlinger et al. |
| 11,231,787 B2 | 1/2022 | Isaacs et al. |
| 11,243,404 B2 | 2/2022 | McDowall et al. |
| 11,244,508 B2 | 2/2022 | Kazanzides et al. |
| 11,253,216 B2 | 2/2022 | Crawford et al. |
| 11,253,323 B2 | 2/2022 | Hughes et al. |
| 11,257,190 B2 | 2/2022 | Mao et al. |
| 11,257,241 B2 | 2/2022 | Tao |
| 11,263,772 B2 | 3/2022 | Siemionow et al. |
| 11,269,401 B2 | 3/2022 | West et al. |
| 11,272,151 B2 | 3/2022 | Casas |
| 11,278,359 B2 | 3/2022 | Siemionow et al. |
| 11,278,413 B1 | 3/2022 | Lang |
| 11,280,480 B2 | 3/2022 | Wilt et al. |
| 11,284,846 B2 | 3/2022 | Graumann et al. |
| 11,291,521 B2 | 4/2022 | Im |
| 11,294,167 B2 | 4/2022 | Ishimoda |
| 11,297,285 B2 | 4/2022 | Pierce |
| 11,300,252 B2 | 4/2022 | Nguyen |
| 11,300,790 B2 | 4/2022 | Cheng et al. |
| 11,304,621 B2 | 4/2022 | Merschon et al. |
| 11,304,759 B2 | 4/2022 | Kovtun et al. |
| 11,307,402 B2 | 4/2022 | Steier et al. |
| 11,308,663 B2 | 4/2022 | Alhrishy et al. |
| 11,311,341 B2 | 4/2022 | Lang |
| 11,317,973 B2 | 5/2022 | Calloway et al. |
| 11,337,763 B2 | 5/2022 | Choi |
| 11,348,257 B2 | 5/2022 | Lang |
| 11,350,072 B1 | 5/2022 | Quiles Casas |
| 11,350,965 B2 | 6/2022 | Yilmaz et al. |
| 11,351,006 B2 | 6/2022 | Aferzon et al. |
| 11,354,813 B2 | 6/2022 | Piat et al. |
| 11,360,315 B2 | 6/2022 | Tu et al. |
| 11,373,342 B2 | 6/2022 | Stafford et al. |
| 11,382,699 B2 | 7/2022 | Wassall et al. |
| 11,382,700 B2 | 7/2022 | Calloway et al. |
| 11,382,712 B2 | 7/2022 | Elimelech et al. |
| 11,382,713 B2 | 7/2022 | Healy et al. |
| 11,389,252 B2 | 7/2022 | Gera et al. |
| 11,393,229 B2 | 7/2022 | Zhou et al. |
| 11,399,895 B2 | 8/2022 | Soper et al. |
| 11,402,524 B2 | 8/2022 | Song et al. |
| 11,406,338 B2 | 8/2022 | Tolkowsky |
| 11,412,202 B2 | 8/2022 | Hegyi |
| 11,423,554 B2 | 8/2022 | Borsdorf et al. |
| 11,430,203 B2 | 8/2022 | Navab et al. |
| 11,432,828 B1 | 9/2022 | Lang |
| 11,432,931 B2 | 9/2022 | Lang |
| 11,443,428 B2 | 9/2022 | Petersen et al. |
| 11,443,431 B2 | 9/2022 | Flossmann et al. |
| 11,452,568 B2 | 9/2022 | Lang |
| 11,452,570 B2 | 9/2022 | Tolkowsky |
| 11,460,915 B2 | 10/2022 | Frielinghaus et al. |
| 11,461,936 B2 | 10/2022 | Freeman et al. |
| 11,461,983 B2 | 10/2022 | Jones et al. |
| 11,464,580 B2 | 10/2022 | Kemp et al. |
| 11,464,581 B2 | 10/2022 | Calloway |
| 11,475,625 B1 | 10/2022 | Douglas |
| 11,478,214 B2 | 10/2022 | Siewerdsen et al. |
| 11,483,532 B2 | 10/2022 | Quiles Casas |
| 11,488,021 B2 | 11/2022 | Sun et al. |
| 11,490,986 B2 | 11/2022 | Ben-Yishai |
| 11,510,750 B2 | 11/2022 | Dulin et al. |
| 11,513,358 B2 | 11/2022 | McDowall et al. |
| 11,527,002 B2 | 12/2022 | Govari |
| 11,528,393 B2 | 12/2022 | Garofolo et al. |
| 11,544,031 B2 | 1/2023 | Harviainen |
| 11,573,420 B2 | 2/2023 | Sarma et al. |
| 11,589,927 B2 | 2/2023 | Oezbek et al. |
| 11,627,924 B2 | 4/2023 | Alexandroni et al. |
| 11,644,675 B2 | 5/2023 | Manly et al. |
| 11,648,016 B2 | 5/2023 | Hathaway et al. |
| 11,651,499 B2 | 5/2023 | Wang et al. |
| 11,657,518 B2 | 5/2023 | Ketcha et al. |
| 11,666,458 B2 | 6/2023 | Kim et al. |
| 11,669,984 B2 | 6/2023 | Siewerdsen et al. |
| 11,686,947 B2 | 6/2023 | Loyola et al. |
| 11,699,236 B2 | 7/2023 | Avital et al. |
| 11,712,582 B2 | 8/2023 | Miyazaki et al. |
| 11,715,210 B2 | 8/2023 | Haslam et al. |
| 11,719,941 B2 | 8/2023 | Russell |
| 11,730,389 B2 | 8/2023 | Farshad et al. |
| 11,733,516 B2 | 8/2023 | Edwin et al. |
| 11,734,901 B2 | 8/2023 | Jones et al. |
| 11,744,657 B2 | 9/2023 | LeBoeuf et al. |
| 11,750,794 B2 | 9/2023 | Benishti et al. |
| 11,766,296 B2 | 9/2023 | Wolf et al. |
| 11,798,178 B2 | 10/2023 | Merlet |
| 11,801,097 B2 | 10/2023 | Crawford et al. |
| 11,801,115 B2 | 10/2023 | Elimelech et al. |
| 11,808,943 B2 | 11/2023 | Robaina et al. |
| 11,815,683 B2 | 11/2023 | Sears et al. |
| 11,826,111 B2 | 11/2023 | Mahfouz |
| 11,832,886 B2 | 12/2023 | Dorman |
| 11,838,493 B2 | 12/2023 | Healy et al. |
| 11,839,433 B2 | 12/2023 | Schaewe et al. |
| 11,839,501 B2 | 12/2023 | Takahashi et al. |
| 11,864,934 B2 | 1/2024 | Junio et al. |
| 11,885,752 B2 | 1/2024 | St-Aubin et al. |
| 11,892,647 B2 | 2/2024 | Hung et al. |
| 11,896,445 B2 | 2/2024 | Gera et al. |
| 11,900,620 B2 | 2/2024 | Lalys et al. |
| 11,914,155 B2 | 2/2024 | Zhu et al. |
| 11,918,310 B1 | 3/2024 | Roh et al. |
| 11,922,631 B2 | 3/2024 | Haslam et al. |
| 11,941,814 B2 | 3/2024 | Crawford et al. |
| 11,944,508 B1 | 4/2024 | Cowin et al. |
| 11,948,265 B2 | 4/2024 | Gibby et al. |
| 11,950,968 B2 | 4/2024 | Wiggermann |
| 11,957,420 B2 | 4/2024 | Lang |
| 11,961,193 B2 | 4/2024 | Pelzl et al. |
| 11,963,723 B2 | 4/2024 | Vilsmeier et al. |
| 11,972,582 B2 | 4/2024 | Yan et al. |
| 11,974,819 B2 | 5/2024 | Finley et al. |
| 11,974,887 B2 | 5/2024 | Elimelech et al. |
| 11,977,232 B2 | 5/2024 | Wu et al. |
| 11,980,429 B2 | 5/2024 | Wolf et al. |
| 11,980,506 B2 | 5/2024 | Wolf et al. |
| 11,980,507 B2 | 5/2024 | Elimelech et al. |
| 11,980,508 B2 | 5/2024 | Elimelech et al. |
| 11,983,824 B2 | 5/2024 | Avisar et al. |
| 12,002,171 B2 | 6/2024 | Jones et al. |
| 12,010,285 B2 | 6/2024 | Quiles Casas |
| 12,014,497 B2 | 6/2024 | Hong et al. |
| 12,019,314 B1 | 6/2024 | Steines et al. |
| 12,033,322 B2 | 7/2024 | Laaksonen et al. |
| 12,044,856 B2 | 7/2024 | Gera et al. |
| 12,044,858 B2 | 7/2024 | Gera et al. |
| 12,056,830 B2 | 8/2024 | Cvetko et al. |
| 12,059,281 B2 | 8/2024 | Weingarten et al. |
| 12,063,338 B2 | 8/2024 | Quiles Casas |
| 12,063,345 B2 | 8/2024 | Benishti et al. |
| 12,069,233 B2 | 8/2024 | Benishti et al. |
| 12,076,158 B2 | 9/2024 | Geiger et al. |
| 12,076,196 B2 | 9/2024 | Elimelech et al. |
| 12,079,385 B2 | 9/2024 | Ben-Yishai et al. |
| 2002/0082498 A1 | 6/2002 | Wendt et al. |
| 2003/0059097 A1 | 3/2003 | Abovitz et al. |
| 2003/0117393 A1 | 6/2003 | Sauer et al. |
| 2003/0130576 A1 | 7/2003 | Seeley et al. |
| 2003/0156144 A1 | 8/2003 | Morita |
| 2003/0210812 A1 | 11/2003 | Khamene et al. |
| 2003/0225329 A1 | 12/2003 | Rossner et al. |
| 2004/0019263 A1 | 1/2004 | Jutras et al. |
| 2004/0030237 A1 | 2/2004 | Lee et al. |
| 2004/0138556 A1 | 7/2004 | Cosman |
| 2004/0152955 A1 | 8/2004 | McGinley et al. |
| 2004/0171930 A1 | 9/2004 | Grimm et al. |
| 2004/0238732 A1 | 12/2004 | State et al. |

(56) References Cited

U.S. PATENT DOCUMENTS

| | | |
|---|---|---|
| 2005/0017972 A1 | 1/2005 | Poole et al. |
| 2005/0024586 A1 | 2/2005 | Teiwes et al. |
| 2005/0119639 A1 | 6/2005 | McCombs et al. |
| 2005/0154296 A1 | 7/2005 | Lechner et al. |
| 2005/0203367 A1 | 9/2005 | Ahmed et al. |
| 2005/0203380 A1 | 9/2005 | Sauer et al. |
| 2005/0215879 A1 | 9/2005 | Chuanggui |
| 2005/0267358 A1 | 12/2005 | Tuma et al. |
| 2006/0072124 A1 | 4/2006 | Smetak et al. |
| 2006/0134198 A1 | 6/2006 | Tawa et al. |
| 2006/0147100 A1 | 7/2006 | Fitzpatrick |
| 2006/0176242 A1 | 8/2006 | Jaramaz et al. |
| 2007/0018975 A1 | 1/2007 | Chuanggui et al. |
| 2007/0058261 A1 | 3/2007 | Sugihara et al. |
| 2007/0100325 A1 | 5/2007 | Jutras et al. |
| 2007/0183041 A1 | 8/2007 | McCloy et al. |
| 2007/0233371 A1 | 10/2007 | Stoschek et al. |
| 2007/0273610 A1 | 11/2007 | Baillot |
| 2008/0002809 A1 | 1/2008 | Bodduluri |
| 2008/0007645 A1 | 1/2008 | McCutchen |
| 2008/0035266 A1 | 2/2008 | Danziger |
| 2008/0085033 A1 | 4/2008 | Haven et al. |
| 2008/0159612 A1 | 7/2008 | Fu et al. |
| 2008/0183065 A1 | 7/2008 | Goldbach |
| 2008/0221625 A1 | 9/2008 | Hufner et al. |
| 2008/0253527 A1 | 10/2008 | Boyden et al. |
| 2008/0262812 A1 | 10/2008 | Arata et al. |
| 2008/0287728 A1 | 11/2008 | Mostafavi et al. |
| 2009/0005961 A1 | 1/2009 | Grabowski et al. |
| 2009/0018437 A1 | 1/2009 | Cooke |
| 2009/0024127 A1 | 1/2009 | Lechner et al. |
| 2009/0036902 A1 | 2/2009 | DiMaio et al. |
| 2009/0062869 A1 | 3/2009 | Claverie et al. |
| 2009/0099445 A1 | 4/2009 | Burger |
| 2009/0123452 A1 | 5/2009 | Madison |
| 2009/0227847 A1 | 9/2009 | Tepper et al. |
| 2009/0285366 A1 | 11/2009 | Essenreiter et al. |
| 2009/0300540 A1 | 12/2009 | Russell |
| 2010/0076305 A1 | 3/2010 | Maier-Hein et al. |
| 2010/0094308 A1 | 4/2010 | Tatsumi et al. |
| 2010/0106010 A1 | 4/2010 | Rubner et al. |
| 2010/0114110 A1 | 5/2010 | Taft et al. |
| 2010/0138939 A1 | 6/2010 | Bentzon et al. |
| 2010/0149073 A1 | 6/2010 | Chaum et al. |
| 2010/0172567 A1 | 7/2010 | Prokoski |
| 2010/0210939 A1 | 8/2010 | Hartmann et al. |
| 2010/0266220 A1 | 10/2010 | Zagorchev et al. |
| 2010/0274124 A1 | 10/2010 | Jascob et al. |
| 2011/0004259 A1 | 1/2011 | Stallings et al. |
| 2011/0098553 A1 | 4/2011 | Robbins et al. |
| 2011/0105895 A1 | 5/2011 | Kornblau et al. |
| 2011/0216060 A1 | 9/2011 | Weising et al. |
| 2011/0245625 A1 | 10/2011 | Trovato et al. |
| 2011/0248064 A1 | 10/2011 | Marczyk |
| 2011/0254922 A1 | 10/2011 | Schaerer et al. |
| 2011/0306873 A1 | 12/2011 | Shenai et al. |
| 2012/0014608 A1 | 1/2012 | Watanabe |
| 2012/0068913 A1 | 3/2012 | Bar-Zeev et al. |
| 2012/0078236 A1 | 3/2012 | Schoepp |
| 2012/0109151 A1 | 5/2012 | Maier-Hein et al. |
| 2012/0143050 A1 | 6/2012 | Heigl |
| 2012/0155064 A1 | 6/2012 | Waters |
| 2012/0162452 A1 | 6/2012 | Liu |
| 2012/0182605 A1 | 7/2012 | Hall et al. |
| 2012/0201421 A1 | 8/2012 | Hartmann et al. |
| 2012/0216411 A1 | 8/2012 | Wevers et al. |
| 2012/0224260 A1 | 9/2012 | Healy et al. |
| 2012/0238609 A1 | 9/2012 | Srivastava et al. |
| 2012/0289777 A1 | 11/2012 | Chopra et al. |
| 2012/0306850 A1 | 12/2012 | Balan et al. |
| 2012/0320100 A1 | 12/2012 | Machida et al. |
| 2013/0002928 A1 | 1/2013 | Imai |
| 2013/0009853 A1 | 1/2013 | Hesselink et al. |
| 2013/0038632 A1 | 2/2013 | Dillavou et al. |
| 2013/0050258 A1 | 2/2013 | Liu et al. |
| 2013/0050833 A1 | 2/2013 | Lewis et al. |
| 2013/0057581 A1 | 3/2013 | Meier |
| 2013/0079829 A1 | 3/2013 | Globerman et al. |
| 2013/0083009 A1 | 4/2013 | Geisner et al. |
| 2013/0106833 A1 | 5/2013 | Fun |
| 2013/0135734 A1 | 5/2013 | Shafer et al. |
| 2013/0135738 A1 | 5/2013 | Shafer et al. |
| 2013/0190602 A1 | 7/2013 | Liao et al. |
| 2013/0195338 A1 | 8/2013 | Xu et al. |
| 2013/0209953 A1 | 8/2013 | Arlinsky et al. |
| 2013/0212453 A1 | 8/2013 | Gudai et al. |
| 2013/0234914 A1 | 9/2013 | Fujimaki |
| 2013/0234935 A1 | 9/2013 | Griffith |
| 2013/0237811 A1 | 9/2013 | Mihailescu et al. |
| 2013/0245461 A1 | 9/2013 | Maier-Hein et al. |
| 2013/0249787 A1 | 9/2013 | Morimoto |
| 2013/0249945 A1 | 9/2013 | Kobayashi |
| 2013/0265623 A1 | 10/2013 | Sugiyama et al. |
| 2013/0267838 A1 | 10/2013 | Fronk et al. |
| 2013/0278631 A1 | 10/2013 | Border et al. |
| 2013/0278635 A1 | 10/2013 | Maggiore |
| 2013/0300637 A1 | 11/2013 | Smits et al. |
| 2013/0300760 A1 | 11/2013 | Sugano et al. |
| 2013/0342571 A1 | 12/2013 | Kinnebrew et al. |
| 2013/0345718 A1 | 12/2013 | Crawford et al. |
| 2014/0031668 A1 | 1/2014 | Mobasser et al. |
| 2014/0049629 A1 | 2/2014 | Siewerdsen et al. |
| 2014/0088402 A1 | 3/2014 | Xu |
| 2014/0088990 A1 | 3/2014 | Nawana et al. |
| 2014/0104505 A1 | 4/2014 | Koenig |
| 2014/0105912 A1 | 4/2014 | Noelle |
| 2014/0114173 A1 | 4/2014 | Bar-Tal et al. |
| 2014/0142426 A1 | 5/2014 | Razzaque et al. |
| 2014/0168261 A1 | 6/2014 | Margolis et al. |
| 2014/0176661 A1 | 6/2014 | Smurro et al. |
| 2014/0177023 A1 | 6/2014 | Gao et al. |
| 2014/0189508 A1 | 7/2014 | Granchi et al. |
| 2014/0198129 A1 | 7/2014 | Liu et al. |
| 2014/0218291 A1 | 8/2014 | Kirk |
| 2014/0240484 A1 | 8/2014 | Kodama et al. |
| 2014/0243614 A1 | 8/2014 | Rothberg et al. |
| 2014/0256429 A1 | 9/2014 | Kobayashi et al. |
| 2014/0266983 A1 | 9/2014 | Christensen |
| 2014/0268356 A1 | 9/2014 | Bolas et al. |
| 2014/0270505 A1 | 9/2014 | McCarthy |
| 2014/0275760 A1 | 9/2014 | Lee et al. |
| 2014/0285404 A1 | 9/2014 | Takano et al. |
| 2014/0285429 A1 | 9/2014 | Simmons |
| 2014/0288413 A1* | 9/2014 | Hwang .................. A61B 34/30 600/407 |
| 2014/0300632 A1 | 10/2014 | Laor |
| 2014/0300967 A1 | 10/2014 | Tilleman et al. |
| 2014/0301624 A1 | 10/2014 | Barckow et al. |
| 2014/0303491 A1 | 10/2014 | Shekhar et al. |
| 2014/0320399 A1 | 10/2014 | Kim et al. |
| 2014/0333899 A1 | 11/2014 | Smithwick |
| 2014/0336461 A1 | 11/2014 | Reiter et al. |
| 2014/0340286 A1 | 11/2014 | Machida et al. |
| 2014/0361956 A1 | 12/2014 | Mikhailov et al. |
| 2014/0371728 A1 | 12/2014 | Vaughn |
| 2015/0005772 A1 | 1/2015 | Anglin et al. |
| 2015/0018672 A1 | 1/2015 | Blumhofer et al. |
| 2015/0031985 A1 | 1/2015 | Reddy et al. |
| 2015/0043798 A1 | 2/2015 | Carrell et al. |
| 2015/0070347 A1 | 3/2015 | Hofmann et al. |
| 2015/0084990 A1 | 3/2015 | Laor |
| 2015/0150641 A1 | 6/2015 | Daon et al. |
| 2015/0182293 A1 | 7/2015 | Yang et al. |
| 2015/0192776 A1 | 7/2015 | Lee et al. |
| 2015/0209119 A1 | 7/2015 | Theodore et al. |
| 2015/0230873 A1 | 8/2015 | Kubiak et al. |
| 2015/0230893 A1 | 8/2015 | Huwais |
| 2015/0261922 A1 | 9/2015 | Nawana et al. |
| 2015/0277123 A1 | 10/2015 | Chaum et al. |
| 2015/0282735 A1 | 10/2015 | Rossner |
| 2015/0287188 A1 | 10/2015 | Gazit et al. |
| 2015/0287236 A1 | 10/2015 | Winne et al. |
| 2015/0297314 A1 | 10/2015 | Fowler et al. |
| 2015/0305828 A1 | 10/2015 | Park et al. |

(56) References Cited

U.S. PATENT DOCUMENTS

| | | |
|---|---|---|
| 2015/0310668 A1 | 10/2015 | Ellerbrock |
| 2015/0338652 A1 | 11/2015 | Lim et al. |
| 2015/0338653 A1 | 11/2015 | Subramaniam et al. |
| 2015/0350517 A1 | 12/2015 | Duret et al. |
| 2015/0351863 A1 | 12/2015 | Plassky et al. |
| 2015/0363978 A1 | 12/2015 | Maimone et al. |
| 2015/0366620 A1 | 12/2015 | Cameron et al. |
| 2016/0015878 A1 | 1/2016 | Graham et al. |
| 2016/0022287 A1 | 1/2016 | Nehls |
| 2016/0030131 A1 | 2/2016 | Yang et al. |
| 2016/0054571 A1 | 2/2016 | Tazbaz et al. |
| 2016/0086380 A1 | 3/2016 | Vayser et al. |
| 2016/0103318 A1 | 4/2016 | Du et al. |
| 2016/0125603 A1 | 5/2016 | Tanji |
| 2016/0133051 A1 | 5/2016 | Aonuma et al. |
| 2016/0143699 A1 | 5/2016 | Tanji |
| 2016/0153004 A1 | 6/2016 | Zhang et al. |
| 2016/0163045 A1 | 6/2016 | Penney et al. |
| 2016/0175064 A1 | 6/2016 | Steinle et al. |
| 2016/0178910 A1 | 6/2016 | Giudicelli et al. |
| 2016/0191887 A1 | 6/2016 | Casas |
| 2016/0223822 A1 | 8/2016 | Harrison et al. |
| 2016/0228033 A1 | 8/2016 | Rossner |
| 2016/0246059 A1 | 8/2016 | Halpin et al. |
| 2016/0249989 A1 | 9/2016 | Devam et al. |
| 2016/0256223 A1 | 9/2016 | Haimerl et al. |
| 2016/0275684 A1 | 9/2016 | Elenbaas et al. |
| 2016/0297315 A1 | 10/2016 | Gonzalez et al. |
| 2016/0302870 A1 | 10/2016 | Wilkinson et al. |
| 2016/0324580 A1 | 11/2016 | Esterberg |
| 2016/0324583 A1 | 11/2016 | Kheradpir et al. |
| 2016/0339337 A1 | 11/2016 | Ellsworth et al. |
| 2017/0014119 A1 | 1/2017 | Capote et al. |
| 2017/0024634 A1 | 1/2017 | Miao et al. |
| 2017/0027650 A1 | 2/2017 | Merck et al. |
| 2017/0031163 A1 | 2/2017 | Gao et al. |
| 2017/0031179 A1 | 2/2017 | Guillot et al. |
| 2017/0045742 A1 | 2/2017 | Greenhalgh et al. |
| 2017/0065364 A1 | 3/2017 | Schuh et al. |
| 2017/0068119 A1 | 3/2017 | Antaki et al. |
| 2017/0076501 A1 | 3/2017 | Jagga et al. |
| 2017/0086941 A1 | 3/2017 | Marti et al. |
| 2017/0112586 A1 | 4/2017 | Dhupar |
| 2017/0164919 A1 | 6/2017 | Lavallee et al. |
| 2017/0164920 A1 | 6/2017 | Lavallee et al. |
| 2017/0178375 A1 | 6/2017 | Benishti et al. |
| 2017/0220224 A1 | 8/2017 | Kodali et al. |
| 2017/0239015 A1 | 8/2017 | Sela et al. |
| 2017/0245944 A1 | 8/2017 | Crawford et al. |
| 2017/0251900 A1 | 9/2017 | Hansen et al. |
| 2017/0252109 A1 | 9/2017 | Yang et al. |
| 2017/0258526 A1 | 9/2017 | Lang |
| 2017/0281283 A1 | 10/2017 | Siegler et al. |
| 2017/0312032 A1 | 11/2017 | Amanatullah et al. |
| 2017/0322950 A1 | 11/2017 | Han et al. |
| 2017/0348055 A1 | 12/2017 | Salcedo et al. |
| 2017/0348061 A1 | 12/2017 | Joshi et al. |
| 2017/0366773 A1 | 12/2017 | Kiraly et al. |
| 2017/0367766 A1 | 12/2017 | Mahfouz |
| 2017/0367771 A1 | 12/2017 | Tako et al. |
| 2017/0372477 A1 | 12/2017 | Penney et al. |
| 2018/0003981 A1 | 1/2018 | Urey |
| 2018/0018791 A1 | 1/2018 | Guoyi |
| 2018/0021597 A1 | 1/2018 | Berlinger et al. |
| 2018/0028266 A1 | 2/2018 | Barnes et al. |
| 2018/0036884 A1 | 2/2018 | Chen et al. |
| 2018/0049622 A1 | 2/2018 | Ryan et al. |
| 2018/0055579 A1 | 3/2018 | Daon et al. |
| 2018/0071029 A1 | 3/2018 | Srimohanarajah et al. |
| 2018/0078316 A1 | 3/2018 | Schaewe et al. |
| 2018/0082480 A1 | 3/2018 | White et al. |
| 2018/0092667 A1 | 4/2018 | Heigl et al. |
| 2018/0092698 A1 | 4/2018 | Chopra et al. |
| 2018/0092699 A1 | 4/2018 | Finley |
| 2018/0116732 A1 | 5/2018 | Lin et al. |
| 2018/0116741 A1 | 5/2018 | Garcia et al. |
| 2018/0117150 A1 | 5/2018 | O'Dwyer et al. |
| 2018/0120106 A1 | 5/2018 | Sato |
| 2018/0133871 A1 | 5/2018 | Farmer |
| 2018/0153626 A1 | 6/2018 | Yang et al. |
| 2018/0182150 A1 | 6/2018 | Benishti et al. |
| 2018/0185100 A1 | 7/2018 | Weinstein et al. |
| 2018/0185113 A1 | 7/2018 | Gregerson et al. |
| 2018/0193097 A1 | 7/2018 | McLachlin et al. |
| 2018/0200002 A1 | 7/2018 | Kostrzewski et al. |
| 2018/0247128 A1 | 8/2018 | Alvi et al. |
| 2018/0262743 A1 | 9/2018 | Casas |
| 2018/0303558 A1 | 10/2018 | Thomas |
| 2018/0311011 A1 | 11/2018 | Van Beek et al. |
| 2018/0317803 A1 | 11/2018 | Ben-Yishai et al. |
| 2018/0318035 A1 | 11/2018 | McLachlin et al. |
| 2018/0368898 A1 | 12/2018 | DiVincenzo et al. |
| 2019/0000372 A1 | 1/2019 | Gullotti et al. |
| 2019/0000564 A1 | 1/2019 | Navab et al. |
| 2019/0015163 A1 | 1/2019 | Abhari et al. |
| 2019/0018235 A1 | 1/2019 | Ouderkirk et al. |
| 2019/0038362 A1 | 2/2019 | Nash et al. |
| 2019/0038365 A1 | 2/2019 | Soper et al. |
| 2019/0043238 A1 | 2/2019 | Benishti et al. |
| 2019/0043392 A1 | 2/2019 | Abele |
| 2019/0046272 A1 | 2/2019 | Zoabi et al. |
| 2019/0046276 A1 | 2/2019 | Inglese et al. |
| 2019/0053851 A1 | 2/2019 | Siemionow et al. |
| 2019/0069971 A1 | 3/2019 | Tripathi et al. |
| 2019/0080515 A1 | 3/2019 | Geri et al. |
| 2019/0105116 A1 | 4/2019 | Johnson et al. |
| 2019/0130792 A1 | 5/2019 | Rios et al. |
| 2019/0142519 A1 | 5/2019 | Siemionow et al. |
| 2019/0144443 A1 | 5/2019 | Jackson et al. |
| 2019/0175228 A1 | 6/2019 | Elimelech et al. |
| 2019/0192230 A1 | 6/2019 | Siemionow et al. |
| 2019/0200894 A1 | 7/2019 | Jung et al. |
| 2019/0201106 A1 | 7/2019 | Siemionow et al. |
| 2019/0205606 A1 | 7/2019 | Zhou et al. |
| 2019/0216537 A1 | 7/2019 | Eltorai et al. |
| 2019/0251692 A1 | 8/2019 | Schmidt-Richberg et al. |
| 2019/0251694 A1 | 8/2019 | Han et al. |
| 2019/0254753 A1 | 8/2019 | Johnson et al. |
| 2019/0273916 A1 | 9/2019 | Benishti et al. |
| 2019/0310481 A1 | 10/2019 | Blum et al. |
| 2019/0333480 A1 | 10/2019 | Lang |
| 2019/0369660 A1 | 12/2019 | Wen et al. |
| 2019/0369717 A1 | 12/2019 | Frielinghaus et al. |
| 2019/0378276 A1 | 12/2019 | Flossmann et al. |
| 2019/0387351 A1 | 12/2019 | Lyren et al. |
| 2020/0015895 A1 | 1/2020 | Frielinghaus et al. |
| 2020/0019364 A1 | 1/2020 | Pond |
| 2020/0020249 A1 | 1/2020 | Jarc et al. |
| 2020/0038112 A1 | 2/2020 | Amanatullah et al. |
| 2020/0043160 A1 | 2/2020 | Mizukura et al. |
| 2020/0078100 A1 | 3/2020 | Weinstein et al. |
| 2020/0085511 A1 | 3/2020 | Oezbek et al. |
| 2020/0088997 A1 | 3/2020 | Lee et al. |
| 2020/0100847 A1 | 4/2020 | Siegler et al. |
| 2020/0117025 A1 | 4/2020 | Sauer |
| 2020/0129058 A1 | 4/2020 | Li et al. |
| 2020/0129136 A1 | 4/2020 | Harding et al. |
| 2020/0129262 A1 | 4/2020 | Verard et al. |
| 2020/0129264 A1 | 4/2020 | Oativia et al. |
| 2020/0133029 A1 | 4/2020 | Yonezawa |
| 2020/0138518 A1 | 5/2020 | Lang |
| 2020/0138618 A1 | 5/2020 | Roszkowiak et al. |
| 2020/0143594 A1 | 5/2020 | Lal et al. |
| 2020/0146546 A1 | 5/2020 | Chene et al. |
| 2020/0151507 A1 | 5/2020 | Siemionow et al. |
| 2020/0156259 A1 | 5/2020 | Ruiz et al. |
| 2020/0159313 A1 | 5/2020 | Gibby et al. |
| 2020/0163723 A1 | 5/2020 | Wolf et al. |
| 2020/0163739 A1 | 5/2020 | Messinger et al. |
| 2020/0178916 A1 | 6/2020 | Lalys et al. |
| 2020/0184638 A1 | 6/2020 | Meglan et al. |
| 2020/0186786 A1 | 6/2020 | Gibby et al. |
| 2020/0188028 A1 | 6/2020 | Feiner et al. |
| 2020/0188034 A1 | 6/2020 | Lequette et al. |

(56) References Cited

U.S. PATENT DOCUMENTS

| | | |
|---|---|---|
| 2020/0201082 A1 | 6/2020 | Carabin |
| 2020/0229877 A1 | 7/2020 | Siemionow et al. |
| 2020/0237256 A1 | 7/2020 | Farshad et al. |
| 2020/0237459 A1 | 7/2020 | Racheli et al. |
| 2020/0237880 A1 | 7/2020 | Kent et al. |
| 2020/0242280 A1 | 7/2020 | Pavloff et al. |
| 2020/0246074 A1 | 8/2020 | Lang |
| 2020/0246081 A1 | 8/2020 | Johnson et al. |
| 2020/0264451 A1 | 8/2020 | Blum et al. |
| 2020/0265273 A1 | 8/2020 | Wei et al. |
| 2020/0275988 A1 | 9/2020 | Johnson et al. |
| 2020/0281554 A1 | 9/2020 | Trini et al. |
| 2020/0286222 A1 | 9/2020 | Essenreiter et al. |
| 2020/0288075 A1 | 9/2020 | Bonin et al. |
| 2020/0294233 A1 | 9/2020 | Merlet |
| 2020/0297427 A1 | 9/2020 | Cameron et al. |
| 2020/0305980 A1 | 10/2020 | Lang |
| 2020/0315734 A1 | 10/2020 | El Amm |
| 2020/0321099 A1 | 10/2020 | Holladay et al. |
| 2020/0323460 A1 | 10/2020 | Busza et al. |
| 2020/0323609 A1 | 10/2020 | Johnson et al. |
| 2020/0327721 A1 | 10/2020 | Siemionow et al. |
| 2020/0330179 A1 | 10/2020 | Ton |
| 2020/0337780 A1 | 10/2020 | Winkler et al. |
| 2020/0341283 A1 | 10/2020 | McCracken et al. |
| 2020/0352655 A1 | 11/2020 | Freese |
| 2020/0355927 A1 | 11/2020 | Marcellin-Dibon et al. |
| 2020/0360091 A1 | 11/2020 | Murray et al. |
| 2020/0375666 A1 | 12/2020 | Murphy |
| 2020/0377493 A1 | 12/2020 | Heiser et al. |
| 2020/0377956 A1 | 12/2020 | Vogelstein et al. |
| 2020/0388075 A1 | 12/2020 | Kazanzides et al. |
| 2020/0389425 A1 | 12/2020 | Bhatia et al. |
| 2020/0390502 A1 | 12/2020 | Holthuizen et al. |
| 2020/0390503 A1 | 12/2020 | Casas et al. |
| 2020/0402647 A1 | 12/2020 | Domracheva et al. |
| 2020/0409306 A1 | 12/2020 | Gelman et al. |
| 2020/0410687 A1 | 12/2020 | Siemionow et al. |
| 2020/0413031 A1 | 12/2020 | Khani et al. |
| 2021/0004956 A1 | 1/2021 | Book et al. |
| 2021/0009339 A1 | 1/2021 | Morrison et al. |
| 2021/0015560 A1 | 1/2021 | Boddington et al. |
| 2021/0015583 A1 | 1/2021 | Avisar et al. |
| 2021/0022599 A1 | 1/2021 | Freeman et al. |
| 2021/0022808 A1 | 1/2021 | Lang |
| 2021/0022811 A1 | 1/2021 | Mahfouz |
| 2021/0022828 A1 | 1/2021 | Elimelech et al. |
| 2021/0029804 A1 | 1/2021 | Chang |
| 2021/0030374 A1 | 2/2021 | Takahashi et al. |
| 2021/0030511 A1 | 2/2021 | Wolf et al. |
| 2021/0038339 A1 | 2/2021 | Yu et al. |
| 2021/0049825 A1 | 2/2021 | Wheelwright et al. |
| 2021/0052348 A1 | 2/2021 | Stifter et al. |
| 2021/0056687 A1 | 2/2021 | Hibbard et al. |
| 2021/0065911 A1 | 3/2021 | Goel et al. |
| 2021/0077195 A1 | 3/2021 | Saeidi et al. |
| 2021/0077210 A1 | 3/2021 | Itkowitz et al. |
| 2021/0080751 A1 | 3/2021 | Lindsey et al. |
| 2021/0090344 A1 | 3/2021 | Geri et al. |
| 2021/0093391 A1 | 4/2021 | Poltaretskyi et al. |
| 2021/0093392 A1 | 4/2021 | Poltaretskyi et al. |
| 2021/0093400 A1 | 4/2021 | Quaid et al. |
| 2021/0093417 A1 | 4/2021 | Liu |
| 2021/0104055 A1 | 4/2021 | Ni et al. |
| 2021/0107923 A1 | 4/2021 | Jackson et al. |
| 2021/0109349 A1 | 4/2021 | Schneider et al. |
| 2021/0109373 A1 | 4/2021 | Loo et al. |
| 2021/0110517 A1 | 4/2021 | Flohr et al. |
| 2021/0113269 A1 | 4/2021 | Vilsmeier et al. |
| 2021/0113293 A9 | 4/2021 | Silva et al. |
| 2021/0121238 A1 | 4/2021 | Palushi et al. |
| 2021/0137634 A1 | 5/2021 | Lang |
| 2021/0141887 A1 | 5/2021 | Kim et al. |
| 2021/0150702 A1 | 5/2021 | Claessen et al. |
| 2021/0157544 A1 | 5/2021 | Denton |
| 2021/0160472 A1 | 5/2021 | Casas |
| 2021/0161614 A1 | 6/2021 | Elimelech et al. |
| 2021/0162287 A1 | 6/2021 | Xing et al. |
| 2021/0165207 A1 | 6/2021 | Peyman |
| 2021/0169504 A1 | 6/2021 | Brown |
| 2021/0169578 A1 | 6/2021 | Calloway et al. |
| 2021/0169581 A1 | 6/2021 | Calloway et al. |
| 2021/0169605 A1 | 6/2021 | Calloway et al. |
| 2021/0186647 A1 | 6/2021 | Elimelech et al. |
| 2021/0196404 A1 | 7/2021 | Wang |
| 2021/0211640 A1 | 7/2021 | Bristol et al. |
| 2021/0223577 A1 | 7/2021 | Zhang et al. |
| 2021/0225006 A1 | 7/2021 | Grady et al. |
| 2021/0227791 A1 | 7/2021 | De Oliveira Seixas et al. |
| 2021/0231301 A1 | 7/2021 | Hikmet et al. |
| 2021/0235061 A1 | 7/2021 | Hegyi |
| 2021/0248822 A1 | 8/2021 | Choi et al. |
| 2021/0274281 A1 | 9/2021 | Zhang et al. |
| 2021/0278675 A1 | 9/2021 | Klug et al. |
| 2021/0282887 A1 | 9/2021 | Wiggermann |
| 2021/0290046 A1 | 9/2021 | Nazareth et al. |
| 2021/0290336 A1 | 9/2021 | Wang |
| 2021/0290394 A1 | 9/2021 | Mahfouz |
| 2021/0295108 A1 | 9/2021 | Bar |
| 2021/0295512 A1 | 9/2021 | Knoplioch et al. |
| 2021/0298795 A1 | 9/2021 | Bowling et al. |
| 2021/0298835 A1 | 9/2021 | Wang |
| 2021/0306599 A1 | 9/2021 | Pierce |
| 2021/0311322 A1 | 10/2021 | Belanger et al. |
| 2021/0314502 A1 | 10/2021 | Liu |
| 2021/0315636 A1 | 10/2021 | Akbarian et al. |
| 2021/0315662 A1 | 10/2021 | Freeman et al. |
| 2021/0325684 A1 | 10/2021 | Ninan et al. |
| 2021/0332447 A1 | 10/2021 | Lubelski et al. |
| 2021/0333561 A1 | 10/2021 | Oh et al. |
| 2021/0341739 A1 | 11/2021 | Cakmakci et al. |
| 2021/0341740 A1 | 11/2021 | Cakmakci et al. |
| 2021/0346115 A1 | 11/2021 | Dulin et al. |
| 2021/0349677 A1 | 11/2021 | Baldev et al. |
| 2021/0364802 A1 | 11/2021 | Uchiyama et al. |
| 2021/0369226 A1 | 12/2021 | Siemionow et al. |
| 2021/0371413 A1 | 12/2021 | Thurston et al. |
| 2021/0373333 A1 | 12/2021 | Moon |
| 2021/0373344 A1 | 12/2021 | Loyola et al. |
| 2021/0378757 A1 | 12/2021 | Bay et al. |
| 2021/0382310 A1 | 12/2021 | Freeman et al. |
| 2021/0386482 A1 | 12/2021 | Gera et al. |
| 2021/0389590 A1 | 12/2021 | Freeman et al. |
| 2021/0400247 A1 | 12/2021 | Casas |
| 2021/0401533 A1 | 12/2021 | Im |
| 2021/0402255 A1 | 12/2021 | Fung |
| 2021/0405369 A1 | 12/2021 | King |
| 2022/0003992 A1 | 1/2022 | Ahn |
| 2022/0007006 A1 | 1/2022 | Healy et al. |
| 2022/0008135 A1 | 1/2022 | Frielinghaus et al. |
| 2022/0038675 A1 | 2/2022 | Hegyi |
| 2022/0039873 A1 | 2/2022 | Harris |
| 2022/0051484 A1 | 2/2022 | Jones et al. |
| 2022/0054199 A1 | 2/2022 | Sivaprakasam et al. |
| 2022/0061921 A1 | 3/2022 | Crawford et al. |
| 2022/0071712 A1 | 3/2022 | Wolf et al. |
| 2022/0079675 A1 | 3/2022 | Lang |
| 2022/0087746 A1 | 3/2022 | Lang |
| 2022/0113810 A1 | 4/2022 | Isaacs et al. |
| 2022/0117669 A1 | 4/2022 | Nikou et al. |
| 2022/0121041 A1 | 4/2022 | Hakim |
| 2022/0133484 A1 | 5/2022 | Lang |
| 2022/0142730 A1 | 5/2022 | Wolf et al. |
| 2022/0155861 A1 | 5/2022 | Myung et al. |
| 2022/0159227 A1 | 5/2022 | Quiles Casas |
| 2022/0179209 A1 | 6/2022 | Cherukuri |
| 2022/0192776 A1 | 6/2022 | Gibby et al. |
| 2022/0193453 A1 | 6/2022 | Miyazaki et al. |
| 2022/0201274 A1 | 6/2022 | Achilefu et al. |
| 2022/0245400 A1 | 8/2022 | Siemionow et al. |
| 2022/0245821 A1 | 8/2022 | Ouzounis |
| 2022/0257206 A1 | 8/2022 | Hartley et al. |
| 2022/0269077 A1 | 8/2022 | Adema et al. |
| 2022/0270263 A1 | 8/2022 | Junio |

(56) References Cited

U.S. PATENT DOCUMENTS

| | | |
|---|---|---|
| 2022/0287676 A1 | 9/2022 | Steines et al. |
| 2022/0292786 A1 | 9/2022 | Pelzl et al. |
| 2022/0295033 A1 | 9/2022 | Quiles Casas |
| 2022/0296315 A1 | 9/2022 | Sokhanvar et al. |
| 2022/0304768 A1 | 9/2022 | Elimelech et al. |
| 2022/0351385 A1 | 11/2022 | Finley et al. |
| 2022/0353487 A1 | 11/2022 | Hegyi |
| 2022/0358759 A1 | 11/2022 | Cork et al. |
| 2022/0370152 A1 | 11/2022 | Lavallee et al. |
| 2022/0387130 A1 | 12/2022 | Spaas et al. |
| 2022/0392085 A1 | 12/2022 | Finley et al. |
| 2022/0397750 A1 | 12/2022 | Zhou et al. |
| 2022/0398752 A1 | 12/2022 | Yoon et al. |
| 2022/0398755 A1 | 12/2022 | Herrmann |
| 2022/0405935 A1 | 12/2022 | Flossmann et al. |
| 2023/0004013 A1 | 1/2023 | McCracken et al. |
| 2023/0009793 A1 | 1/2023 | Gera et al. |
| 2023/0025480 A1 | 1/2023 | Kemp et al. |
| 2023/0027801 A1 | 1/2023 | Qian et al. |
| 2023/0032731 A1 | 2/2023 | Hrndler et al. |
| 2023/0034189 A1 | 2/2023 | Gera et al. |
| 2023/0050636 A1 | 2/2023 | Yanof et al. |
| 2023/0053120 A1 | 2/2023 | Jamali et al. |
| 2023/0073041 A1 | 3/2023 | Samadani et al. |
| 2023/0085387 A1 | 3/2023 | Jones et al. |
| 2023/0087783 A1 | 3/2023 | Dulin et al. |
| 2023/0100078 A1 | 3/2023 | Toporek et al. |
| 2023/0123621 A1 | 4/2023 | Joshi et al. |
| 2023/0126207 A1 | 4/2023 | Wang |
| 2023/0129056 A1 | 4/2023 | Hemingway et al. |
| 2023/0131515 A1 | 4/2023 | Oezbek et al. |
| 2023/0149083 A1 | 5/2023 | Lin et al. |
| 2023/0162493 A1 | 5/2023 | Worrell et al. |
| 2023/0165640 A1 | 6/2023 | Dulin et al. |
| 2023/0169659 A1 | 6/2023 | Chen et al. |
| 2023/0196582 A1 | 6/2023 | Grady et al. |
| 2023/0200917 A1 | 6/2023 | Calloway et al. |
| 2023/0236426 A1 | 7/2023 | Manly et al. |
| 2023/0236427 A1 | 7/2023 | Chen |
| 2023/0260142 A1 | 8/2023 | Chatterjee et al. |
| 2023/0290037 A1 | 9/2023 | Tasse et al. |
| 2023/0295302 A1 | 9/2023 | Bhagavatheeswaran et al. |
| 2023/0306590 A1 | 9/2023 | Jazdzyk et al. |
| 2023/0316550 A1 | 10/2023 | Hiasa |
| 2023/0326011 A1 | 10/2023 | Cutforth et al. |
| 2023/0326027 A1 | 10/2023 | Wahrenberg |
| 2023/0329799 A1 | 10/2023 | Gera et al. |
| 2023/0329801 A1 | 10/2023 | Elimelech et al. |
| 2023/0334664 A1 | 10/2023 | Lu et al. |
| 2023/0335261 A1 | 10/2023 | Reicher et al. |
| 2023/0359043 A1 | 11/2023 | Russell |
| 2023/0363832 A1 | 11/2023 | Mosadegh et al. |
| 2023/0371984 A1 | 11/2023 | Leuthardt et al. |
| 2023/0372053 A1 | 11/2023 | Elimelech et al. |
| 2023/0372054 A1 | 11/2023 | Elimelech et al. |
| 2023/0377171 A1 | 11/2023 | Hasler et al. |
| 2023/0377175 A1 | 11/2023 | Seok |
| 2023/0379448 A1 | 11/2023 | Benishti et al. |
| 2023/0379449 A1 | 11/2023 | Benishti et al. |
| 2023/0386022 A1 | 11/2023 | Tan et al. |
| 2023/0386067 A1 | 11/2023 | De Nigris et al. |
| 2023/0386153 A1 | 11/2023 | Rybnikov et al. |
| 2023/0394791 A1 | 12/2023 | Wang et al. |
| 2023/0397349 A1 | 12/2023 | Capelli et al. |
| 2023/0397957 A1 | 12/2023 | Crawford et al. |
| 2023/0410445 A1 | 12/2023 | Elimelech et al. |
| 2023/0419496 A1 | 12/2023 | Wuelker et al. |
| 2023/0420114 A1 | 12/2023 | Scholler et al. |
| 2024/0008935 A1 | 1/2024 | Wolf et al. |
| 2024/0016549 A1 | 1/2024 | Johnson et al. |
| 2024/0016572 A1 | 1/2024 | Elimelech et al. |
| 2024/0020831 A1 | 1/2024 | Johnson et al. |
| 2024/0020840 A1 | 1/2024 | Johnson et al. |
| 2024/0020862 A1 | 1/2024 | Johnson et al. |
| 2024/0022704 A1 | 1/2024 | Benishti et al. |
| 2024/0023946 A1 | 1/2024 | Wolf et al. |
| 2024/0041530 A1 | 2/2024 | Lang |
| 2024/0041558 A1 | 2/2024 | Siewerdsen et al. |
| 2024/0045491 A1 | 2/2024 | Sourov |
| 2024/0058064 A1 | 2/2024 | Weiser et al. |
| 2024/0062387 A1 | 2/2024 | Frantz et al. |
| 2024/0103271 A1 | 3/2024 | Zare Seisan |
| 2024/0103282 A1 | 3/2024 | Law et al. |
| 2024/0111163 A1 | 4/2024 | Law et al. |
| 2024/0122560 A1 | 4/2024 | Junio et al. |
| 2024/0126087 A1 | 4/2024 | Gera et al. |
| 2024/0127559 A1 | 4/2024 | Rybnikov et al. |
| 2024/0127578 A1 | 4/2024 | Hiasa |
| 2024/0129451 A1 | 4/2024 | Healy et al. |
| 2024/0130826 A1 | 4/2024 | Elimelech et al. |
| 2024/0134206 A1 | 4/2024 | Gera et al. |
| 2024/0144497 A1 | 5/2024 | Cvetko et al. |
| 2024/0156532 A1 | 5/2024 | Weiman et al. |
| 2024/0177445 A1 | 5/2024 | Galeotti et al. |
| 2024/0177458 A1 | 5/2024 | Zhang et al. |
| 2024/0180634 A1 | 6/2024 | Mikus |
| 2024/0184119 A1 | 6/2024 | Lee et al. |
| 2024/0185509 A1 | 6/2024 | Kovler et al. |
| 2024/0202926 A1 | 6/2024 | Crawford et al. |
| 2024/0202927 A1 | 6/2024 | Haslam et al. |
| 2024/0212111 A1 | 6/2024 | Genghi et al. |
| 2024/0233131 A1 | 7/2024 | Westerhoff et al. |
| 2024/0245463 A1 | 7/2024 | Vilsmeier et al. |
| 2024/0245474 A1 | 7/2024 | Weiman et al. |
| 2024/0248530 A1 | 7/2024 | Gibby et al. |
| 2024/0252252 A1 | 8/2024 | Lang |
| 2024/0261036 A1 | 8/2024 | Finley et al. |
| 2024/0261058 A1 | 8/2024 | Gera et al. |
| 2024/0265645 A1 | 8/2024 | Papar |
| 2024/0266033 A1 | 8/2024 | Freeman et al. |
| 2024/0268922 A1 | 8/2024 | Calloway et al. |
| 2024/0273740 A1 | 8/2024 | Gibby et al. |
| 2024/0281979 A1 | 8/2024 | Schrempf et al. |
| 2024/0296527 A1 | 9/2024 | Nett et al. |
| 2024/0303832 A1 | 9/2024 | Chen et al. |
| 2024/0307101 A1 | 9/2024 | Gera et al. |
| 2024/0312012 A1 | 9/2024 | Li et al. |
| 2024/0341910 A1 | 10/2024 | Wolf et al. |
| 2024/0341911 A1 | 10/2024 | Elimelech et al. |

FOREIGN PATENT DOCUMENTS

| | | |
|---|---|---|
| CN | 101379412 A | 3/2009 |
| CN | 103106348 A | 5/2013 |
| CN | 111915696 A | 11/2020 |
| CN | 112489047 A | 3/2021 |
| DE | 202004011567 U1 | 11/2004 |
| DE | 102004011567 A1 | 9/2005 |
| DE | 102014008153 A1 | 10/2014 |
| DE | 202022103168 U1 | 6/2022 |
| EP | 0933096 A2 | 8/1999 |
| EP | 1640750 A1 | 3/2006 |
| EP | 1757974 A1 | 2/2007 |
| EP | 2119397 A1 | 11/2009 |
| EP | 2134847 A2 | 12/2009 |
| EP | 2557998 A1 | 2/2013 |
| EP | 2823463 A1 | 1/2015 |
| EP | 2868277 A1 | 5/2015 |
| EP | 2891966 A1 | 7/2015 |
| EP | 2963616 A2 | 1/2016 |
| EP | 3028258 A1 | 6/2016 |
| EP | 3034607 A1 | 6/2016 |
| EP | 3037038 A1 | 6/2016 |
| EP | 3069318 A1 | 9/2016 |
| EP | 3076660 A1 | 10/2016 |
| EP | 3121789 A1 | 1/2017 |
| EP | 3123970 A1 | 2/2017 |
| EP | 2654749 B1 | 5/2017 |
| EP | 3175815 A1 | 6/2017 |
| EP | 3216416 A1 | 9/2017 |
| EP | 2032039 B1 | 10/2017 |
| EP | 3224376 A1 | 10/2017 |
| EP | 3247297 A1 | 11/2017 |
| EP | 3256213 A1 | 12/2017 |

(56) References Cited

FOREIGN PATENT DOCUMENTS

| | | |
|---|---|---|
| EP | 3306567 A1 | 4/2018 |
| EP | 3320874 A1 | 5/2018 |
| EP | 2030193 B1 | 7/2018 |
| EP | 2225723 B1 | 2/2019 |
| EP | 2619622 B1 | 2/2019 |
| EP | 2892558 B1 | 4/2019 |
| EP | 3494903 A1 | 6/2019 |
| EP | 2635299 B1 | 7/2019 |
| EP | 3505050 A1 | 7/2019 |
| EP | 2875149 B1 | 12/2019 |
| EP | 3593227 A1 | 1/2020 |
| EP | 3634294 A1 | 4/2020 |
| EP | 3206583 B1 | 9/2020 |
| EP | 3711700 A1 | 9/2020 |
| EP | 2625845 B1 | 3/2021 |
| EP | 3789965 A1 | 3/2021 |
| EP | 3858280 A1 | 8/2021 |
| EP | 3913423 A1 | 11/2021 |
| EP | 3952331 A1 | 2/2022 |
| EP | 3960235 A1 | 3/2022 |
| EP | 3635683 B1 | 7/2022 |
| EP | 3602492 B1 | 11/2022 |
| EP | 4173590 A1 | 5/2023 |
| EP | 3533031 B1 | 8/2023 |
| EP | 4252695 A1 | 10/2023 |
| EP | 3195257 B1 | 11/2023 |
| EP | 3405909 B1 | 11/2023 |
| EP | 4270313 A1 | 11/2023 |
| EP | 4287120 A1 | 12/2023 |
| EP | 3488381 B1 | 2/2024 |
| EP | 3834768 B1 | 2/2024 |
| EP | 3903714 B1 | 2/2024 |
| EP | 4336450 A1 | 3/2024 |
| EP | 3814984 B1 | 4/2024 |
| EP | 4115389 B1 | 4/2024 |
| EP | 3752981 B1 | 5/2024 |
| EP | 4375948 A1 | 5/2024 |
| EP | 4383203 A1 | 6/2024 |
| GB | 2507314 A | 4/2014 |
| IL | 262864 A | 3/2019 |
| JP | 2004-237092 A | 8/2004 |
| JP | 2008-507361 A | 3/2008 |
| JP | 2009-514571 A | 4/2009 |
| JP | 2021-525186 A | 9/2021 |
| KR | 10-2014-0120155 A | 10/2014 |
| WO | 03/34705 A2 | 4/2003 |
| WO | 2006/002559 A1 | 1/2006 |
| WO | 2007/051304 A1 | 5/2007 |
| WO | 2007/115826 A2 | 10/2007 |
| WO | 2008/103383 A1 | 8/2008 |
| WO | 2010/067267 A1 | 6/2010 |
| WO | 2010/074747 A1 | 7/2010 |
| WO | 2012/061537 A2 | 5/2012 |
| WO | 2012/101286 A1 | 8/2012 |
| WO | 2013/112554 A1 | 8/2013 |
| WO | 2014/014498 A1 | 1/2014 |
| WO | 2014/024188 A1 | 2/2014 |
| WO | 2014/037953 A2 | 3/2014 |
| WO | 2014/113455 A1 | 7/2014 |
| WO | 2014/125789 A1 | 8/2014 |
| WO | 2014/167563 A1 | 10/2014 |
| WO | 2014/174067 A1 | 10/2014 |
| WO | 2015/058816 A1 | 4/2015 |
| WO | 2015/061752 A1 | 4/2015 |
| WO | 2015/109145 A1 | 7/2015 |
| WO | 2016/151506 A1 | 9/2016 |
| WO | WO-2017042171 A1 * | 3/2017 |
| WO | 2018/052966 A1 | 3/2018 |
| WO | 2018/073452 A1 | 4/2018 |
| WO | 2018/200767 A1 | 11/2018 |
| WO | 2018/206086 A1 | 11/2018 |
| WO | 2019/083431 A1 | 5/2019 |
| WO | 2019/135209 A1 | 7/2019 |
| WO | 2019/161477 A1 | 8/2019 |
| WO | 2019/195926 A1 | 10/2019 |
| WO | 2019/210353 A1 | 11/2019 |
| WO | 2019/211741 A1 | 11/2019 |
| WO | 2020/109903 A1 | 6/2020 |
| WO | 2020/109904 A1 | 6/2020 |
| WO | 2021/017019 A1 | 2/2021 |
| WO | 2021/019369 A1 | 2/2021 |
| WO | 2021/021979 A2 | 2/2021 |
| WO | 2021/023574 A1 | 2/2021 |
| WO | 2021/046455 A1 | 3/2021 |
| WO | 2021/048158 A1 | 3/2021 |
| WO | 2021/061459 A1 | 4/2021 |
| WO | 2021/062375 A1 | 4/2021 |
| WO | 2021/073743 A1 | 4/2021 |
| WO | 2021/087439 A1 | 5/2021 |
| WO | 2021/091980 A1 | 5/2021 |
| WO | 2021/112918 A1 | 6/2021 |
| WO | 2021/130564 A1 | 7/2021 |
| WO | 2021/137752 A1 | 7/2021 |
| WO | 2021/141887 A1 | 7/2021 |
| WO | 2021/145584 A1 | 7/2021 |
| WO | 2021/154076 A1 | 8/2021 |
| WO | 2021/183318 A2 | 9/2021 |
| WO | 2021/188757 A1 | 9/2021 |
| WO | 2021/255627 A1 | 12/2021 |
| WO | 2021/257897 A1 | 12/2021 |
| WO | 2021/258078 A1 | 12/2021 |
| WO | 2022/009233 A1 | 1/2022 |
| WO | 2022/053923 A1 | 3/2022 |
| WO | 2022/079565 A1 | 4/2022 |
| WO | 2023/003952 A1 | 1/2023 |
| WO | 2023/281395 A1 | 1/2023 |
| WO | 2023/007418 A1 | 2/2023 |
| WO | 2023/011924 A1 | 2/2023 |
| WO | 2023/021448 A1 | 2/2023 |
| WO | 2023/021450 A1 | 2/2023 |
| WO | 2023/021451 A1 | 2/2023 |
| WO | 2023/026229 A1 | 3/2023 |
| WO | 2023/047355 A1 | 3/2023 |
| WO | 2023/072887 A1 | 5/2023 |
| WO | 2023/088986 A1 | 5/2023 |
| WO | 2023/158878 A1 | 8/2023 |
| WO | 2023/159104 A2 | 8/2023 |
| WO | 2023/161848 A1 | 8/2023 |
| WO | 2023/163933 A1 | 8/2023 |
| WO | 2023/175244 A1 | 9/2023 |
| WO | 2023/186996 A1 | 10/2023 |
| WO | 2023/202909 A1 | 10/2023 |
| WO | 2023/205212 A1 | 10/2023 |
| WO | 2023/205896 A1 | 11/2023 |
| WO | 2023/209014 A1 | 11/2023 |
| WO | 2023/229415 A1 | 11/2023 |
| WO | 2023/232492 A1 | 12/2023 |
| WO | 2023/240912 A1 | 12/2023 |
| WO | 2024/001140 A1 | 1/2024 |
| WO | 2024/002620 A1 | 1/2024 |
| WO | 2024/013642 A2 | 1/2024 |
| WO | 2024/018368 A2 | 1/2024 |
| WO | 2024/046760 A1 | 3/2024 |
| WO | 2024/052136 A1 | 3/2024 |
| WO | 2024/077077 A1 | 4/2024 |
| WO | 2024/121060 A1 | 6/2024 |
| WO | 2024/132609 A1 | 6/2024 |
| WO | 2024/145341 A1 | 7/2024 |
| WO | 2024/160896 A1 | 8/2024 |
| WO | 2024/165508 A1 | 8/2024 |
| WO | 2024/173251 A1 | 8/2024 |
| WO | 2024/186811 A1 | 9/2024 |

OTHER PUBLICATIONS

U.S. Appl. No. 16/159,740 U.S. Pat. No. 10,382,748, filed Oct. 15, 2018 Aug. 13, 2019, Combining Video-based and Optic-based Augmented Reality in a Near Eye Display.

U.S. Appl. No. 16/419,023 U.S. Pat. No. 11,750,794, filed May 22, 2019 Sep. 5, 2023, Combinging Video-based and Optic-based Augmented Reality in a Near Eye Display.

U.S. Appl. No. 18/352,158, filed Jul. 13, 2023, Combining Video-based and Optic-based Augmented Reality in a Near Eye Display.

(56) References Cited

OTHER PUBLICATIONS

U.S. Appl. No. 18/365,643 U.S. Pat. No. 12,069,233, filed Aug. 4, 2023 Aug. 20, 2024, Head-Mounted Augmented Reality Near Eye Display Device.
U.S. Appl. No. 18/365,650 U.S. Pat. No. 12,063,345, filed Aug. 4, 2023 Aug. 13, 2024, Systems for Facilitating Augmented Reality-assisted Medical Procedures.
U.S. Appl. No. 15/127,423 U.S. Pat. No. 9,928,629, filed Sep. 20, 2016 Mar. 27, 2018, Combining Video-based and Optic-based Augmented Reality in a Near Eye Display.
U.S. Appl. No. 16/120,480 U.S. Pat. No. 10,835,296, filed Sep. 4, 2018 Nov. 17, 2020, Spinous Process Clamp.
U.S. Appl. No. 17/067,831, filed Oct. 12, 2020, Spinous Process Clamp.
U.S. Appl. No. 18/030,072, filed Apr. 4, 2023, Spinous Process Clamp.
U.S. Appl. No. 18/365,590 U.S. Pat. No. 11,980,508, filed Aug. 4, 2023 May 14, 2024, Registration of a Fiducial Marker for an Augmented Reality System.
U.S. Appl. No. 18/365,571 U.S. Pat. No. 11,974,887, filed Aug. 4, 2023 May 7, 2024, Registration Marker for an Augmented Reality System.
U.S. Appl. No. 18/632,588, filed Apr. 11, 2024, Registration of a Fiducial Marker for an Augmented Reality System.
U.S. Appl. No. 17/045,766 U.S. Pat. No. 11,980,507, filed Oct. 7, 2020 May 14, 2024, Registration of a Fiducial Marker for an Augmented Reality System.
U.S. Appl. No. 16/199,281 U.S. Pat. No. 10,939,977, filed Nov. 26, 2018 Mar. 9, 2021, Positioning Marker.
U.S. Appl. No. 16/524,258 U.S. Pat. No. 11,980,506, filed Jul. 29, 2019 May 14, 2024, Fiducial Marker.
U.S. Appl. No. 18/631,804, filed Apr. 10, 2024, Fiducial Marker.
U.S. Appl. No. 17/585,629, filed Jan. 27, 2022, Fiducial Marker.
U.S. Appl. No. 16/724,297 U.S. Pat. No. 11,382,712, filed Dec. 22, 2019 Jul. 12, 2022, Mirroring in Image Guided Surgery.
U.S. Appl. No. 17/827,710 U.S. Pat. No. 11,801,115, filed May 29, 2022 Oct. 31, 2023, Mirroring in Image Guided Surgery.
U.S. Appl. No. 18/352,181, filed Jul. 13, 2023, Mirroring in Image Guided Surgery.
U.S. Appl. No. 18/400,739 U.S. Pat. No. 12,076,196, filed Dec. 29, 2023 Sep. 3, 2024, Mirroring in Image Guided Surgery.
U.S. Appl. No. 18/780,095, filed Jul. 22, 2024, Mirroring in Image Guided Surgery.
U.S. Appl. No. 16/200,144 U.S. Pat. No. 11,766,296, filed Nov. 26, 2018 Sep. 26, 2023, Tracking System for Image-guided Surgery.
U.S. Appl. No. 18/470,809 U.S. Pat. No. 11,980,429, filed Sep. 20, 2023 May 14, 2024, Tracking Methods for Image-guided Surgery.
U.S. Appl. No. 17/015,199, filed Sep. 9, 2020, Universal Tool Adapter.
U.S. Appl. No. 18/598,965, filed Mar. 7, 2024, Universal Tool Adapter for Image Guided Surgery.
U.S. Appl. No. 18/044,380, filed Mar. 8, 2023, Universal Tool Adapter for Image-guided Surgery.
U.S. Appl. No. 16/901,026 U.S. Pat. No. 11,389,252, filed Jun. 15, 2020 Jul. 19, 2022, Rotating Marker for Image Guided Surgery.
U.S. Appl. No. 18/008,980, filed Dec. 8, 2022, Rotating Marker.
U.S. Appl. No. 17/368,859 U.S. Pat. No. 11,896,445, filed Jul. 7, 2021 Feb. 13, 2024, Iliac Pin and Adapter.
U.S. Appl. No. 18/437,898, filed Feb. 9, 2024, Iliac Pin and Adapter.
U.S. Appl. No. 18/576,516, filed Jan. 4, 2024, Iliac Pin and Adapter.
U.S. Appl. No. 17/388,064, filed Jul. 29, 2021, Rotating Marker and Adapter for Image-guided Surgery.
U.S. Appl. No. 18/291,731, filed Jan. 24, 2024, Rotating Marker and Adapter for Image-guided Surgery.
U.S. Appl. No. 18/930,558, filed Oct. 29, 2024, Rotating Marker and Adapter for Image-guided Surgery.
U.S. Appl. No. 18/365,844, filed Aug. 4, 2023, Augmented-reality Surgical System Using Depth Sensing.
U.S. Appl. No. 18/683,676, filed Feb. 14, 2024, Stereoscopic Display and Digital Loupe for Augmented-reality Near-eye Display.
U.S. Appl. No. 18/683,680, filed Feb. 14, 2024, Augmented Reality Assistance for Osteotomy and Discectomy.
U.S. Appl. No. 18/684,756, filed Feb. 19, 2024, Registration and Registration Validation in Image-guided Surgery.
U.S. Appl. No. 18/693,338, filed Mar. 19, 2024, Surgical Planning and Display.
U.S. Appl. No. 18/365,566, filed Aug. 4, 2023, Systems for Medical Image Visualization.
U.S. Appl. No. 18/399,253, filed Dec. 28, 2023, Methods for Medical Image Visualization.
U.S. Appl. No. 18/857,558, filed Oct. 17, 2024, Reduction of Jitter in Virtual Presentation.
U.S. Appl. No. 18/398,837 U.S. Pat. No. 12,044,858, filed Dec. 28, 2023 Jul. 23, 2024, Adjustable Augmented Reality Eyewear for Image-guided Medical Intervention.
U.S. Appl. No. 18/399,433 U.S. Pat. No. 12,044,856, filed Dec. 28, 2023 Jul. 23, 2024, Configurable Augmented Reality Eyewear for Image-guided Medical Intervention.
U.S. Appl. No. 18/772,578, filed Jul. 15, 2024, Augmented Reality Eyewear for Image-guided Medical Intervention.
U.S. Appl. No. 35/508,942 U.S. Pat. No. D. 930,162, filed Feb. 13, 2020 Sep. 7, 2021, Medical Headset.
U.S. Appl. No. 16/159,740 U.S. Pat. No. 10,382,748, filed Oct. 15, 2018 Aug. 13, 2019, Combing Video-based and Optic-based Augmented Reality in a Near Eye Display.
U.S. Appl. No. 16/419,023 U.S. Pat. No. 11,750,794, filed May 22, 2019 Sep. 5, 2023, Combining Video-based and Optic-based Augmented Reality in a Near Eye Display.
U.S. Appl. No. 18/632,588, filed Apr. 11, 2024, Registration of Fiducial Marker for an Augmented Reality System.
U.S. Appl. No. 18/365,643, filed Aug. 4, 2023, Head-mounted Augmented Reality Near Eye Display Device.
U.S. Appl. No. 18/365,650, filed Aug. 4, 2023, Systems for Facilitating Augmented Reality-assisted Medical Procedures.
U.S. Appl. No. 16/524,258 (U.S. Pat. No. 11,980,506), filed Jul. 29, 2019 (May 14, 2024), Fiducial Marker.
U.S. Appl. No. 18/400,739, filed Dec. 29, 2023, Mirroring in Image Guided Surgery.
U.S. Appl. No. 18/398,837, filed Dec. 28, 2023, Adjustable Augmented Reality Eyewear for Image-guided Medical Intervention.
U.S. Appl. No. 18/399,433, filed Dec. 28, 2023, Configurable Augmented Reality Eyewear for Image-guided Medical Intervention.
16 Augmented Reality Glasses of 2021 (with Features), in Back to News, Dated May 6, 2022, accessed at https://web.archive.org/web/20221127195438/https://circuitstream.com/blog/16-augmented-reality-glasses-of-2021-with-features-breakdowns/.
Everysight, Installing your RX Adaptor, accessed Mar. 13, 2024 at https://support.everysight.com/hc/en-us/articles/115000984571-Installing-your-RX-Adaptor.
Everysight, Raptor User Manual, copyright 2017, in 46 pages.
Frames Direct, InSpatialRx Prescription Insert, Prescription Insert for Magic Leap 1, accessed Mar. 8, 2024 at https://www.framesdirect.com/inspatialrx-prescription-insert.html.
Reddit, Notice on Prescription Lenses for Nreal Glasses, accessed Mar. 13, 2024 at https://www.reddit.com/r/nreal/comments/x1fte5/notice_on_prescription_lenses_for_nreal_glasses/.
Vuzix Blades, Prescription Lens Installation Guide, copyright 2020.

* cited by examiner

TRACKING SYSTEMS AND METHODS FOR IMAGE-GUIDED SURGERY

CROSS-REFERENCE TO RELATED APPLICATIONS

This application is a continuation of U.S. patent application Ser. No. 18/470,809, filed Sep. 20, 2023, which is a continuation of U.S. patent application Ser. No. 16/200,144, filed Nov. 26, 2018. Each of the foregoing applications is hereby incorporated by reference herein in its entirety.

FIELD OF EMBODIMENTS OF THE INVENTION

The present invention relates to generally to an augmented reality system, and specifically to a tracking system for an augmented reality system that is used to perform image-guided surgery.

BACKGROUND

A head-mounted display is sometimes used as part of an augmented reality system. The display is used to generate an augmented reality scene, in which a scene that is being viewed by a user of the head-mounted display is altered, typically by being augmented or supplemented. The alteration is computer generated, and typically involves presenting real-time video, and/or non-real-time images, to the user while the user is gazing at the scene.

In some cases, an augmented reality system is used for performing image-guided surgery, as part of a medical procedure. For example, a computer-generated image may be presented to a healthcare professional who is performing the procedure. The image may be presented on a head-mounted display such that the image is aligned with an anatomical portion of a patient who is undergoing the procedure. Although some misalignment of the image with the patient's body may be acceptable, for satisfactory presentation of the images the misalignment may typically not be more than about 2-3 mm. In order to account for such a limit on the misalignment of the patient's anatomy with the presented images, the position of the patient's body or a portion thereof is typically tracked.

In some cases, an image of a tool that is used to perform the procedure is incorporated into the image that is displayed on the head-mounted display. In order to incorporate an image of the tool into the image, in a manner in which the position of the tool with respect to the image and/or the patient's anatomy is accurately reflected, the position of the tool or a portion thereof is typically tracked.

Triangulation techniques are commonly employed for tracking positions of a patient's body and/or a tool. In such techniques, a plurality of imaging devices, which are disposed at known locations with respect to each other, are used to detect a feature (such as a marker) on the patient's body, and/or on the tool. The location of the feature is then derived, using a combination of the known locations of the imaging devices, as well as the location of the feature as detected by each of the imaging devices.

Summary of Embodiments

In accordance with some applications of the present invention, a first healthcare professional (e.g., a surgeon performing a procedure) wears a first head-mounted device. Typically, the head-mounted device includes one or more head-mounted displays. For some applications, the head-mounted displays are generally similar to those described in U.S. Pat. No. 9,928,629 to Benishti, which is incorporated herein by reference. For example, the head-mounted displays may include a combiner that is controlled by a computer processor, such as to display an augmented reality image to the healthcare professional. For some applications, the image is presented on the head-mounted display such that (a) a computer-generated image is projected onto a first portion of the display, and (b) the computer-generated image is aligned with an anatomical portion of a patient who is undergoing the procedure, with the anatomical portion of a patient visible through a second portion of the display. Typically, the computer-generated image includes a virtual image of the tool overlaid upon a virtual image of the patient's anatomy. For some applications, a portion of the tool that would not otherwise be visible to the healthcare professional (for example, by virtue of being hidden by the patient's anatomy) is included in the computer-generated image.

Typically, the head-mounted device includes a tracking device that is configured to facilitate determination of the location and orientation of the head-mounted device with respect to a portion of the patient's body (e.g., the patient's back), and/or the position and orientation of the tool with respect to the patient's body. For example, the tracking device may include an image-capturing device, such as a camera, that is configured to image a patient marker and/or a tool marker. Typically, the patient marker is configured to provide data that is sufficient for the computer processor to determine the location and orientation of the head-mounted device with respect to the portion of the patient's body using data collected from a single tracking device that is disposed on the head-mounted display. For example, the patient marker may include an array of elements that is visible to the tracking device of the head-mounted device, and that is configured such that at any location and orientation of the head-mounted device with respect to the patient marker, the array of elements has an appearance that is unique to that location and orientation. In this manner, the computer processor is able to determine the location and orientation of the head-mounted device with respect to the portion of the patient's body without requiring the use of triangulation techniques. Typically, a single camera is used in the tracking device of the head-mounted device. For some applications, the camera is a high-speed camera. For example, the camera may acquire more than 50 frames per second.

Typically, in order to generate the augmented reality image upon the head-mounted display, a computer processor determines the location and orientation of the head-mounted device with respect to a portion of the patient's body (e.g., the patient's back), and/or the position and orientation of the tool with respect to the portion of the patient's body. As described hereinabove, in general, the patient marker is configured to provide data that is sufficient for the computer processor to determine the location and orientation of the head-mounted device with respect to the portion of the patient's body using data collected from a single tracking device that is disposed on the head-mounted device. However, for some applications, at least under certain conditions, the computer processor is configured to incorporate tracking data that is received from at least one additional tracking device (i.e., a tracking device in addition to the tracking device that is included in the head-mounted device of the first healthcare professional), in order to generate the image upon the head-mounted display of the first healthcare professional.

For some such applications, the computer processor is configured to incorporate the additional data in cases in which the first tracking device that is included in the head-mounted device of the first healthcare professional loses its line of sight with the patient marker and/or the tool marker and/or portions thereof. For example, the computer processor may be configured to receive data from a tracking device of an additional head-mounted device that is configured to be worn by an additional healthcare professional who is present in the procedure (e.g., an accompanying surgeon or a nurse). Typically, the additional head-mounted device is generally similar to the first head-mounted device, and the tracking device of the additional head-mounted device is generally similar to that of the first head-mounted device. For some applications, when at least a portion of the patient marker and a portion of the tool (e.g., the tool marker) are both within the line of sight of the first tracking device, the computer processor generates an augmented reality image upon the head-mounted display, based upon data received from first tracking device and without using data received from the additional tracking device. When at least the portion of the patient marker and the portion of the tool are not both within the line of sight of the first tracking device, the computer processor generates an augmented reality image upon the first head-mounted display, at least partially based upon data received from the additional tracking device.

There is therefore provided, in accordance with some applications of the present invention, a method for use with a tool configured to be placed within a portion of a body of a patient, the method including:
 tracking at least a portion of the tool and a patient marker that is placed upon the patient's body from a first line of sight, using a first tracking device that is disposed upon a first head-mounted device that is worn by a first person, the first head-mounted device including a first head-mounted display;
 tracking at least the portion of the tool and the patient marker, from a second line of sight, using a second tracking device; and
 using at least one computer processor:
  when at least a portion of the patient marker and the portion of the tool are both within the first line of sight, generating an augmented reality image upon the first head-mounted display based upon data received from the first tracking device and without using data from the second tracking device, the augmented reality image including (a) a virtual image of the tool and anatomy of the patient, overlaid upon (b) the patient's body; and
  when at least the portion of the patient marker and the portion of the tool are not both within the first line of sight, generating a virtual image of the tool and anatomy of the patient upon the first head-mounted display, at least partially based upon data received from the second tracking device.

In some applications, tracking the portion of the tool includes tracking a tool marker. In some applications, tracking at least the portion of the tool and the patient marker, from the second line of sight, using the second tracking device, includes tracking at least the portion of the tool and the patient marker from the second line of sight, using a second tracking device that is disposed in a stationary position. In some applications, tracking at least the portion of the tool and the patient marker using the first tracking device includes tracking at least the portion of the tool and the patient marker using a first camera, and tracking at least the portion of the tool and the patient marker using the second tracking device includes tracking at least the portion of the tool and the patient marker using a second camera.

In some applications, generating the virtual image of the tool and anatomy of the patient upon the first head-mounted display, at least partially based upon data received from the second tracking device includes:
 in response to the portion of the patient marker being within the first line of sight, and the portion of the tool not being within the first line of sight:
  determining a position of the tool with respect to the subject's anatomy using data received from the second tracking device;
  generating the virtual image of the tool and anatomy of the patient upon the first head-mounted display, based upon the determined position of the tool with respect to the subject's anatomy;
  determining a position of the patient's body with respect to the first head-mounted device based upon data received from the first tracking device; and
  overlaying the virtual image upon the patient's body, based upon the determined position of the patient's body with respect to the first head-mounted device.

In some applications, generating the virtual image of the tool and anatomy of the patient upon the first head-mounted display, at least partially based upon data received from the second tracking device includes:
 in response to the portion of the tool being within the first line of sight, and the portion of the patient marker not being within the first line of sight:
  determining a position of the tool with respect to the subject's anatomy using data received from the second tracking device;
  generating the virtual image of the tool and anatomy of the patient upon the first head-mounted display, based upon the determined position of the tool with respect to the subject's anatomy.

In some applications, generating the virtual image of the tool and anatomy of the patient upon the first head-mounted display further includes overlaying the virtual image upon the patient's body, based upon a position of the patient's body with respect to the first head-mounted device as determined based upon data received from the first tracking device at a time when the portion of the patient marker was within the first line of sight.

In some applications, overlaying the virtual image upon the patient's body includes tracking movements of the head-mounted device between the time when the portion of the patient marker was within the first line of sight and the portion of the patient marker not being within the first line of sight, using an inertial-measurement unit disposed upon the first head-mounted device.

In some applications, generating the virtual image of the tool and anatomy of the patient upon the first head-mounted display, at least partially based upon data received from the second tracking device includes:
 in response to the portion of the tool and the portion of the patient marker both not being within the first line of sight:
  determining a position of the tool with respect to the subject's anatomy using data received from the second tracking device;
  generating the virtual image of the tool and anatomy of the patient upon the first head-mounted display, based upon the determined position of the tool with respect to the subject's anatomy.

In some applications, generating the virtual image of the tool and anatomy of the patient upon the first head-mounted display further includes overlaying the virtual image upon the patient's body, based upon a position of the patient's body with respect to the first head-mounted device as determined based upon data received from the first tracking device at a time when the portion of the patient marker was within the first line of sight. In some applications, overlaying the virtual image upon the patient's body includes tracking movements of the head-mounted device between the time when the portion of the patient marker was within the first line of sight and the portion of the patient marker not being within the first line of sight, using an inertial-measurement unit disposed upon the first head-mounted device.

In some applications, tracking at least the portion of the tool and the patient marker, from the second line of sight, using the second tracking device, includes tracking at least the portion of the tool and the patient marker from the second line of sight, using a second tracking device that is disposed upon a second head-mounted device that is worn by a second person. In some applications, the second head-mounted device includes a second head-mounted display, the method further including generating a further augmented-reality image upon the second head-mounted display.

There is further provided, in accordance with some applications of the present invention, apparatus for use with a tool configured to be placed within a portion of a body of a patient, the apparatus including:
- a patient marker configured to be placed upon the patient's body;
- a first head-mounted device including a first head-mounted display, and a first tracking device that is configured to track at least a portion of the tool and the patient marker from a first line of sight;
- a second tracking device that is configured to track at least the portion of the tool and the patient marker from a second line of sight; and
- at least one computer processor configured:
  - when at least a portion of the patient marker and the portion of the tool are both within the first line of sight, to generate an augmented reality image upon the first head-mounted display, based upon data received from the first tracking device and without using data from the second tracking device, the augmented reality image including (a) a virtual image of the tool and anatomy of the patient, overlaid upon (b) the patient's body; and
  - when at least the portion of the patient marker and the portion of the tool are not both within the first line of sight, to generate a virtual image of the tool and anatomy of the patient upon the first head-mounted display, at least partially based upon data received from the second tracking device.

There is further provided, in accordance with some applications of the present invention, a method for use with a tool configured to be placed within a portion of a body of a patient, the method including:
- tracking at least a portion of the tool and a patient marker that is placed upon the patient's body from a first line of sight, using a first tracking device that is disposed upon a first head-mounted device that is worn by a first person, the first head-mounted device including a first head-mounted display;
- tracking at least the portion of the tool and the patient marker from a second line of sight, using a second tracking device that is disposed upon a second head-mounted device that is worn by a second person; and
- using at least one computer processor, generating an augmented reality image upon the first head-mounted display, based upon data received from the first tracking device in combination with data received from the second tracking device, the augmented reality image including (a) a virtual image of the tool and anatomy of the patient, overlaid upon (b) the patient's body.

In some applications, tracking the portion of the tool includes tracking a tool marker. In some applications, the second head-mounted device includes a second head-mounted display, the method further including generating a further augmented-reality image upon the second head-mounted display. In some applications, tracking at least the portion of the tool and the patient marker using the first tracking device includes tracking at least the portion of the tool and the patient marker using a first camera, and tracking at least the portion of the tool and the patient marker using the second tracking device includes tracking at least the portion of the tool and the patient marker using a second camera.

In some applications, generating the augmented reality image upon the first head-mounted display includes:
- determining a position of the tool with respect to the subject's anatomy using data received from the first tracking device in combination with data received from the second tracking device;
- generating the virtual image of the tool and anatomy of the patient upon the first head-mounted display, based upon the determined position of the tool with respect to the subject's anatomy;
- determining a position of the patient's body with respect to the first head-mounted device based upon data received from the first tracking device; and
- overlaying the virtual image upon the patient's body, based upon the determined position of the patient's body with respect to the first head-mounted device.

There is further provided, in accordance with some applications of the present invention, apparatus for use with a tool configured to be placed within a portion of a body of a patient, the apparatus including:
- a patient marker configured to be placed upon the patient's body;
- a first head-mounted device configured to be worn by a first person, the first head-mounted device including a first head-mounted display, and a first tracking device that is configured to track at least a portion of the tool and the patient marker from a first line of sight;
- a second head-mounted device configured to be worn by a second person, the second head-mounted device including a second tracking device that is configured to track at least a portion of the tool and the patient marker from a second line of sight; and
- at least one computer processor configured to generate an augmented reality image upon the first head-mounted display, based upon data received from the first tracking device in combination with data received from the second tracking device, the augmented reality image including (a) a virtual image of the tool and anatomy of the patient, overlaid upon (b) the patient's body.

The present invention will be more fully understood from the following detailed description of applications thereof, taken together with the drawings, in which:

DETAILED DESCRIPTION OF EMBODIMENTS

Figure 1:
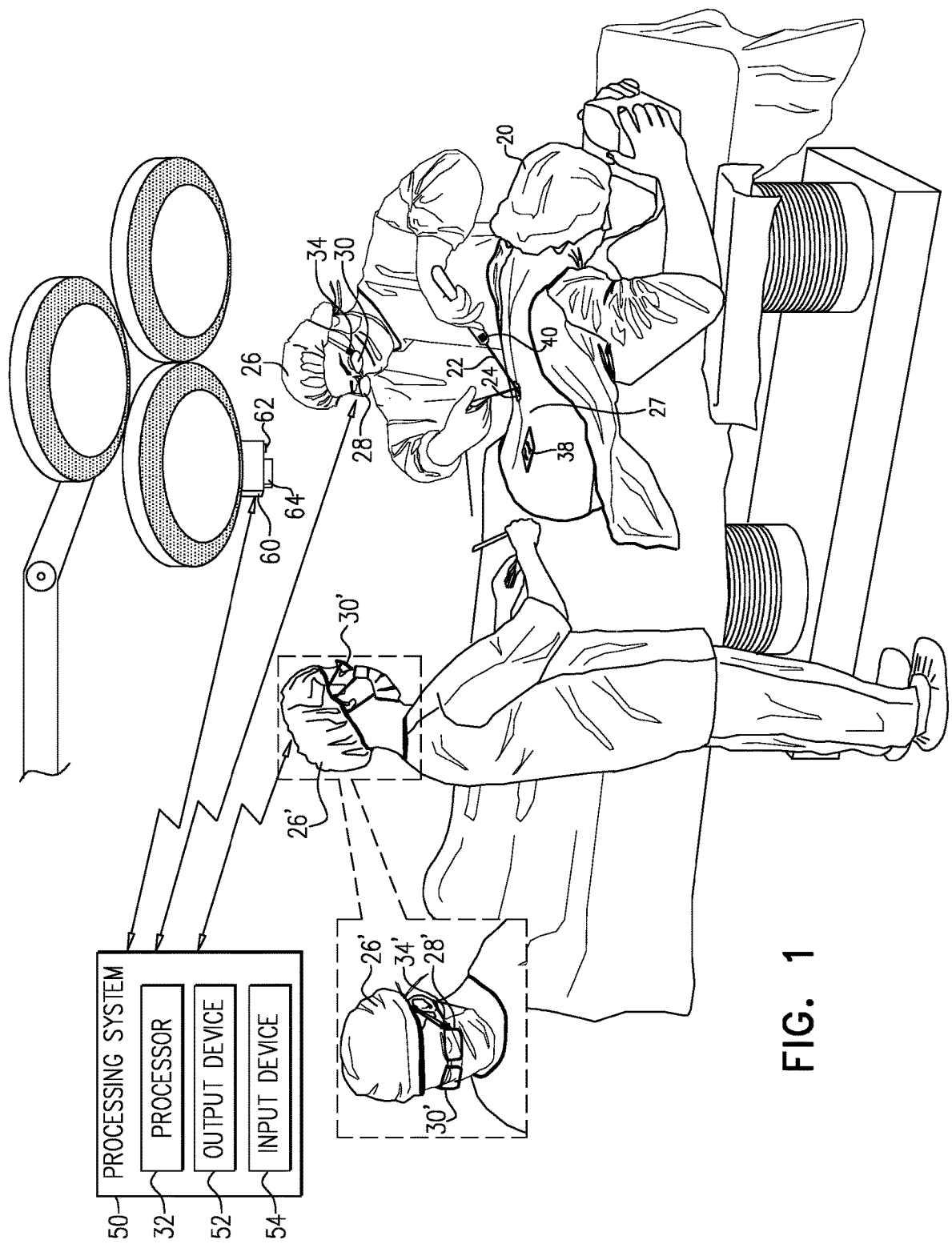
FIG. 1 is a schematic illustration of image-guided surgery being performed upon a patient, in accordance with some applications of the present invention.
Figure 2:
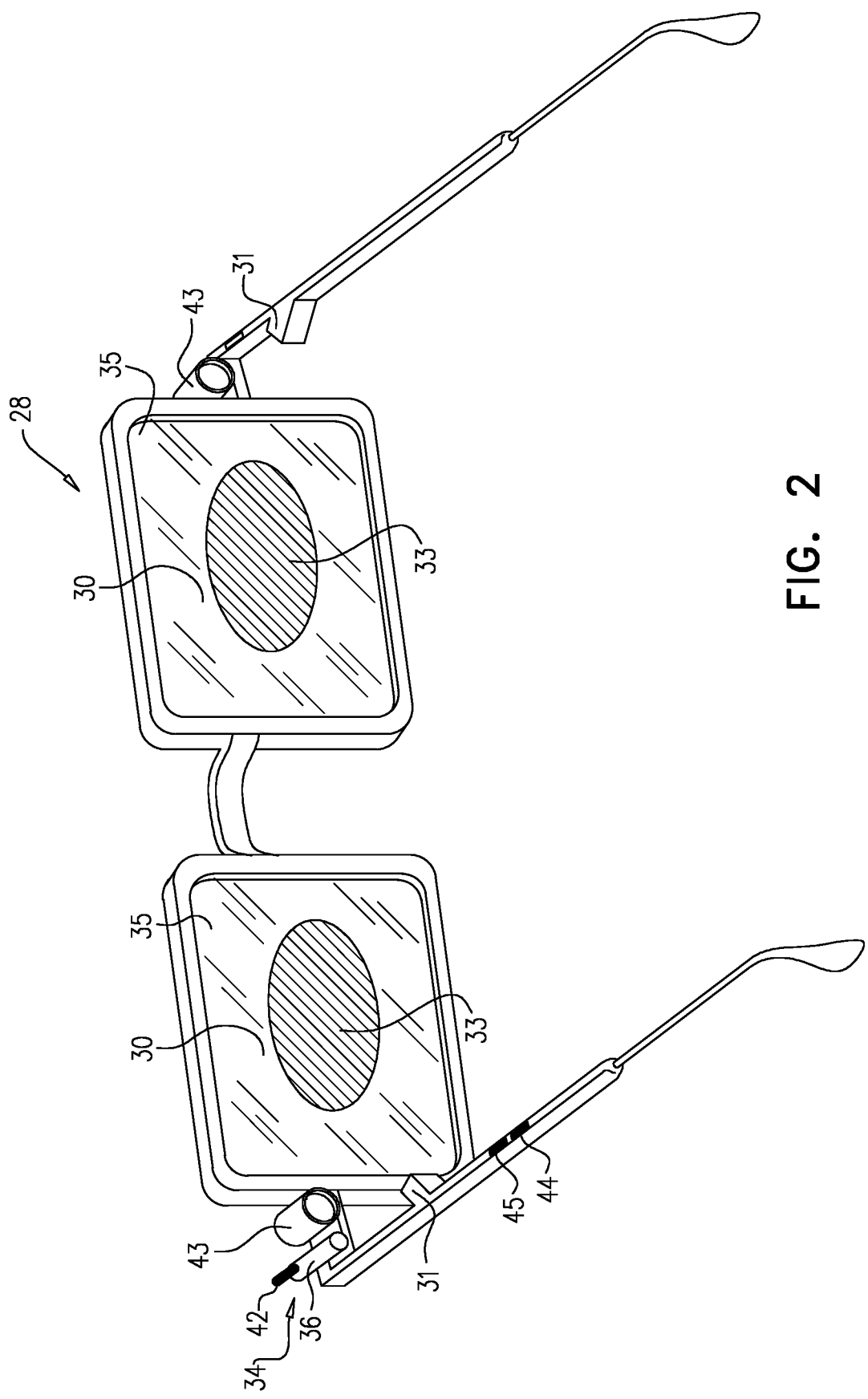
FIG. 2 is a schematic illustration of a head-mounted device, in accordance with some applications of the present invention.

Reference is now made to FIG. 1, which is a schematic illustration of a medical procedure that incorporates image-guided surgery being performed upon a patient 20, in accordance with some applications of the present invention. In the medical procedure shown in FIG. 1, a tool 22 is used to perform an action with respect to the patient's back, the tool being inserted via an incision 24 on the patient's back 27. However, the apparatus and techniques described herein may be used in any surgical procedure that is performed upon a patient's body, mutatis mutandis. Reference is also made to FIG. 2, which is a schematic illustration of a head-mounted device 28, in accordance with some applications of the present invention.

For some applications, a first healthcare professional 26 (e.g., a surgeon performing the procedure) wears a first head-mounted device 28. Typically, the head-mounted device includes one or more head-mounted displays 30. For some applications, the head-mounted displays are generally similar to those described in U.S. Pat. No. 9,928,629 to Benishti, which is incorporated herein by reference. For example, the head-mounted displays may include a combiner that is controlled by a computer processor (e.g., computer processor 32 and/or computer processor 45 described hereinbelow), such as to display an augmented reality image to the healthcare professional. For some applications, the image is presented on head-mounted display 30 such that (a) a computer-generated image is projected onto a first portion 33 of the display by projector 31, and (b) the computer-generated image is aligned with an anatomical portion of a patient who is undergoing the procedure, with the anatomical portion of a patient being visible through a second portion 35 of the display. Typically, the computer-generated image includes a virtual image of the tool overlaid upon a virtual image of the patient's anatomy. For some applications, a portion of the tool that would not otherwise be visible to the healthcare professional (for example, by virtue of being hidden by the patient's anatomy) is included in the computer-generated image.

Although some misalignment of the image with the patient's body may be acceptable, for satisfactory presentation of the images the misalignment may typically not be more than about 2-3 mm. In order to account for such a limit on the misalignment of the patient's anatomy with the presented images, the position of the patient's body, or a portion thereof, with respect to the head-mounted device is typically tracked. In some cases, an image of a tool that is used to perform the procedure is incorporated into the image that is displayed on the head-mounted display. In order to incorporate an image of the tool into the image, in a manner in which the position of the tool with respect to the patient's anatomy is accurately reflected, the position of the tool or a portion thereof (e.g., the tool marker) is typically tracked. It is typically desirable to determine the location of the tool with respect to the patient's body such that errors in the determined location of the tool with respect to the patient's body are less than 2 mm.

Typically, head-mounted device 28 includes a tracking device 34 that is configured to facilitate determination of the location and orientation of head-mounted device 28 with respect to a portion of the patient's body (e.g., the patient's back) and/or with respect to tool 22, and/or the position and orientation of the tool with respect to the portion of the patient's body. For example, the tracking device may include an image-capturing device 36, such as a camera, that is configured to image a patient marker 38 and/or a tool marker 40. Typically, a single camera is used in the tracking device of the head-mounted device. For some applications, the camera is a high-speed camera. For example, the camera may acquire more than 50 frames per second.

For some applications, tracking device 34 includes a light source 42, which is mounted on the head-mounted device. The light source is typically configured to irradiate the patient marker and/or the tool marker, such that light reflects from the markers toward the camera. For some applications, image-capturing device 36 is a monochrome camera that includes a filter that is configured to only allow light to pass through that is of a similar wavelength to the light that is generated by the light source. For example, the light source may be an infrared light source (for example, a light source that generates light at a wavelength of between 700 nm and 1000 nm (e.g., between 700 nm and 800 nm)), and the camera may include a corresponding infrared filter. For some applications, an inertial-measurement unit 44 (e.g., an inertial-measurement unit configured to measure in 6 degrees-of-freedom) is disposed on the head-mounted device, as described in further detail hereinbelow. For some applications, the head-mounted device includes additional cameras 43, which are configured to capture images of scenes in the visible spectrum, as described in U.S. Pat. No. 9,928,629 to Benishti, which is incorporated herein by reference. For some applications, head-mounted device 28 includes additional components, for example, as described in U.S. Pat. No. 9,928,629 to Benishti, which is incorporated herein by reference.

Typically, in order to generate an augmented reality image upon display 30, a computer processor determines the location and orientation of head-mounted device 28 with respect to a portion of the patient's body (e.g., the patient's back), and/or the position and orientation of the tool with respect to the patient's body. For example, a computer processor 45 that is integrated within the head-mounted device may perform the aforementioned functionalities. Alternatively or additionally, computer processor 32, which is disposed externally to the head-mounted device and is typically in wireless communication with the head-mounted device may be used to perform these functionalities. Computer processor 32 typically comprises a portion of a processing system 50 that is used with the head-mounted device in order to facilitate the image-guided surgery. For some applications, the processing system additionally includes an output device 52 (e.g., a display, such as a monitor) for outputting information to an operator of the system, and/or an input device 54 (such as a pointing device, a keyboard, a mouse, etc.) configured to allow the operator to input data into the system. In general, in the context of the present application, when a computer processor is described as performing certain steps, these steps may be performed by external computer processor 32, and/or computer processor 45 that is integrated within the head-mounted device.

For some applications, the patient marker and/or the tool marker includes reflective elements that are configured to reflect light that is generated by light source 42. For some such applications, the location and orientation of a portion of the subject's body (e.g., the subject's back) with respect to the head-mounted device is tracked, by directing light from light source 42 toward a region of interest in which the patient marker is disposed. Alternatively or additionally, the location and orientation of the tool with respect to the portion of the subject's body, is tracked by directing light from light source 42 toward a region of interest in which the patient marker and/or the tool marker is disposed. Typically, image-capturing device 36 is disposed upon the head-mounted device in close proximity to the light source, such that the image-capturing device is configured to capture light that is retro-reflected from the patient marker and/or the tool marker.

As described hereinabove, for some applications, the image-capturing device is a monochrome camera that includes a filter that is configured to only allow light to pass through that is of a similar wavelength to the light that is generated by the light source. For such applications, the camera typically receives a grayscale image showing the reflective elements of the tool marker and/or the patient marker. Typically, the computer processor determines the location of a portion of the subject's body (e.g., the subject's back) with respect to the head-mounted device by analyzing the images acquired by the image-capturing device. Further typically, the computer processor determines the location and orientation of the tool with respect to the portion of the subject's body, by analyzing the images acquired by the image-capturing device.

It is noted that the above-described technique for tracking the patient marker and/or the tool marker is presented by way of example, and that for some applications, alternative techniques are used for tracking the patient marker and/or the tool marker. For example, the patient marker and/or the tool marker may include light-absorbing elements, and/or light-generating elements, and the image-capturing device may be configured to track the patient marker and/or the tool marker by detecting these elements. Alternatively or additionally, a different type of detector may be used for tracking the patient marker and/or the tool marker.

Typically, the patient marker is configured to provide data that is sufficient for the computer processor to determine the location and orientation of the head-mounted device with respect to the portion of the patient's body using data collected from a single tracking device that is disposed on the head-mounted display. For example, the patient marker may include an array of elements that is visible to the tracking device of the head-mounted device, and that is configured such that at any location and orientation of the head-mounted device with respect to the patient marker, the array of elements has an appearance that is unique to that location and orientation. In this manner, the computer processor is able to determine the location and orientation of the head-mounted device with respect to the portion of the patient's body without requiring the use of triangulation techniques.

As described in the above paragraph, in general, the patient marker is configured to provide data that is sufficient for the computer processor to determine the location and orientation of the head-mounted device with respect to the portion of the patient's body using data collected from a single tracking device that is disposed on the head-mounted display. However, for some applications, at least under certain circumstances, the computer processor is configured to incorporate tracking data that is received from an additional tracking device (i.e., an additional tracking device to first tracking device 34), in order to generate the image upon head-mounted display 30 of first head-mounted device 28 of first healthcare professional 26.

For some such applications, the computer processor is configured to incorporate the additional data in cases in which tracking device 34 loses its line of sight with the patient marker and/or the tool marker and/or portions thereof. An example of this is shown in FIG. 1, which shows that the right hand of first healthcare professional 26 is blocking the line of sight of his/her tracking device 34 with respect to patient marker 38. For some applications, in such cases, the computer processor is configured to receive data from a tracking device 34' of an additional head-mounted device 28' that is configured to be worn by an additional healthcare professional 26' who is present in the procedure (e.g., an accompanying surgeon, or a nurse), e.g., as shown in FIG. 1. Typically, the additional head-mounted device 28' is generally similar to the first head-mounted device 28, and the tracking device 34' of the additional head-mounted device is generally similar to that of the first head-mounted device. For some applications, when at least a portion of the patient marker and a portion of the tool (e.g., the tool marker) are both within the line of sight of the first tracking device 34, the computer processor generates an augmented reality image upon the head-mounted display 30, based upon data received from first tracking device 34 and without using data received from tracking device 34'. When at least the portion of the patient marker and the portion of the tool are not both within the line of sight of first tracking device 34, the computer processor generates an augmented reality image upon head-mounted display 30, at least partially based upon data received from second tracking device 34'.

Alternatively or additionally, a tracking device 60, which is not mounted on a head-mounted device, is disposed in the operating room. Typically, tracking device 60 is disposed in a stationary position within the operating room. For example, tracking device 60 may be ceiling-mounted, wall-mounted, and/or disposed on a stand, such as a tripod. For some applications, tracking device 60 includes a light source 62 and an image-capturing device 64, which function in a generally similar manner to that described hereinabove with reference to light source 42 and image-capturing device 36.

Figure 3A:
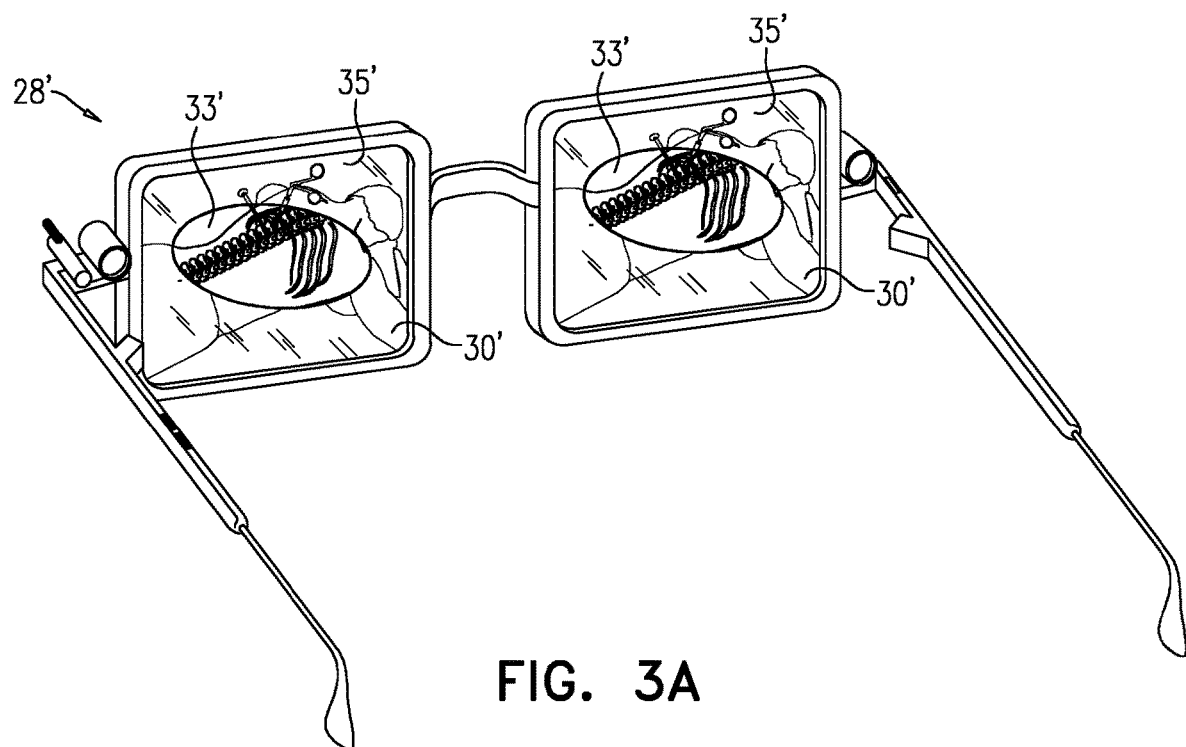
FIGS. 3A and 3B are schematic illustrations of examples of displays of head-mounted devices as worn by respective healthcare professionals, in accordance with some applications of the present invention.
Figure 3B:
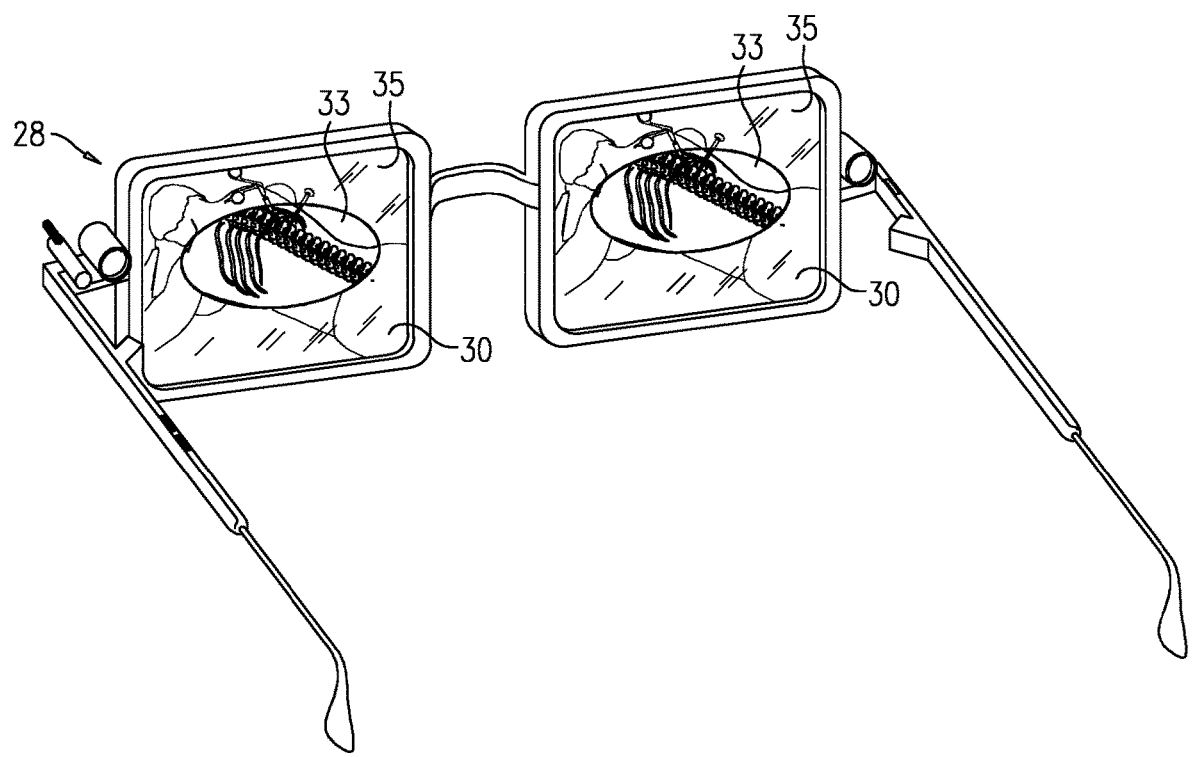

Reference is now made to FIGS. 3A and 3B, which are schematic illustration of examples of displays 30', 30 of head-mounted devices 28', 28 as worn by respective healthcare professionals 26', 26, in accordance with some applications of the present invention. FIG. 3A shows an example of displays 30' of second healthcare professional 26', who is shown on the right side of the patient in FIG. 1, and FIG. 3B shows an example of displays 30 of first healthcare professional 26, who is shown on the left side of the patient in FIG.

1. Typically, the image that is generated upon each of head-mounted displays 30 and head-mounted displays 30' is an augmented-reality view showing virtual patient anatomy aligned with the actual patient anatomy and a virtual tool aligned with the virtual anatomy. As described hereinabove, for some applications, the virtual tool and virtual anatomy are displayed upon a first portion 33 of head-mounted display 30, 30', and the actual patient anatomy is visible through a second portion 35 of head-mounted display 30, 30'. For some applications, the computer processor is configured to generate such a view both in 2D and 3D. In order to generate such a view, it is typically necessary to track the location and orientation of the head-mounted device relative to the patient, in order to correctly align the virtual anatomy with the actual patient anatomy. FIGS. 3A and 3B show how the respective head-mounted displays typically appear, when tracking devices 34 of each of the healthcare professionals has a clear line of sight of the patient marker.

Figure 4A:
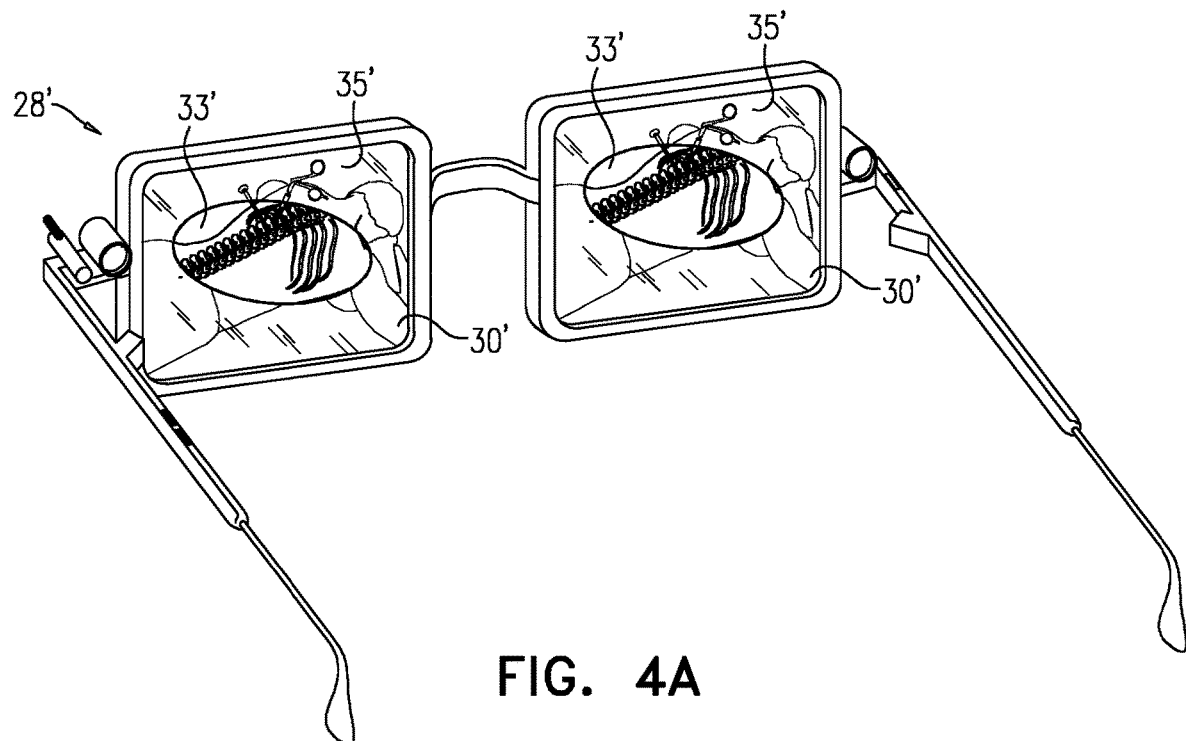
FIGS. 4A and 4B are schematic illustrations of examples of displays of head-mounted devices as worn by respective healthcare professionals, when the line of sight between a tracking device of one of the healthcare professionals with respect to a patient marker is at least partially blocked, in accordance with some applications of the present invention.
Figure 4B:
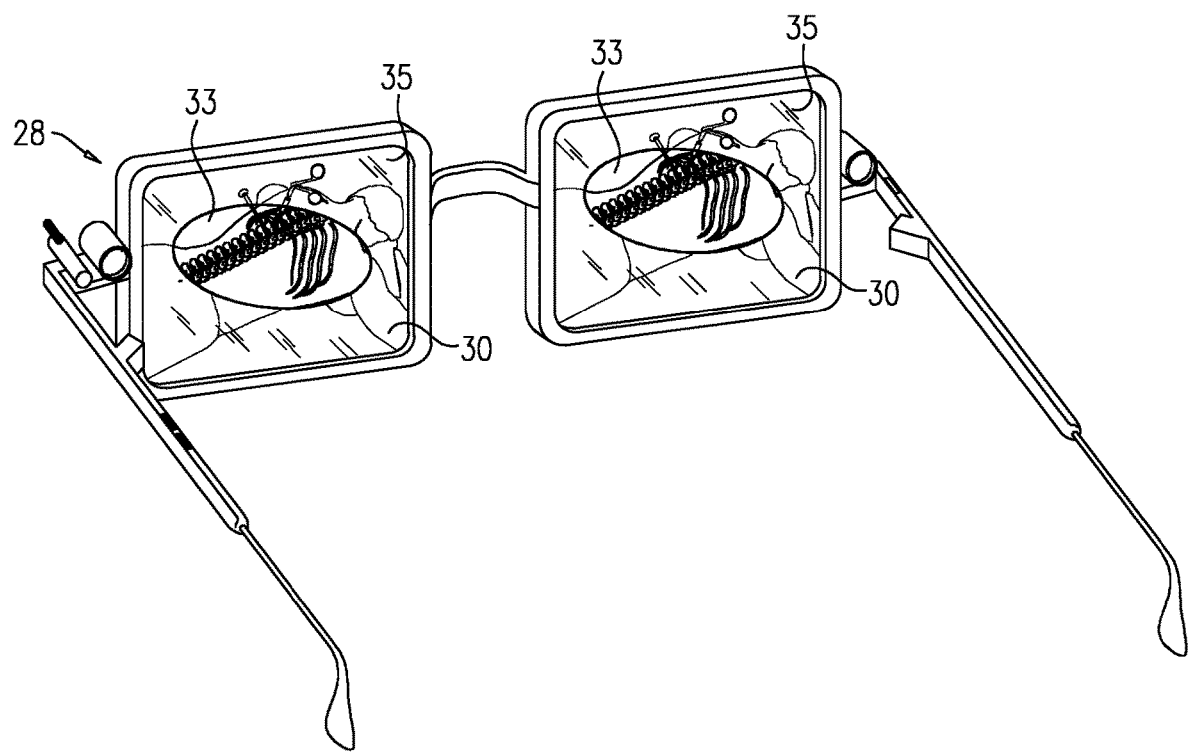

Reference is now made to FIGS. 4A and 4B, which are schematic illustration of examples of displays 30', 30 of head-mounted devices 28', 28 as worn by respective healthcare professionals 26', 26, when the line of sight between tracking device 34 of first healthcare professional 26 with respect to patient marker 38 is at least partially blocked, in accordance with some applications of the present invention. FIG. 4A shows an example of display 30' of second healthcare professional 26', who is shown on the right side of the patient in FIG. 1, and FIG. 4B shows an example of display 30 of first healthcare professional 26, who is shown on the left side of the patient in FIG. 1.

For some such applications, the computer processor generates a virtual image upon head-mounted display 30 of first healthcare professional 26 that shows the virtual view of the second healthcare professional 26' (i.e., the second healthcare professional's view of the virtual anatomy and the virtual tool), as determined based upon the data received from second tracking device 34'. For example, the overall view of the second healthcare professional (including both his/her view of the virtual anatomy and the virtual tool, as well as his/her view of the actual patient anatomy) may be displayed upon head-mounted display 30 of the first healthcare professional. Such an example is shown in FIGS. 4A and 4B, which show the head-mounted displays 30 of first healthcare professional 26 showing the same overall view as that of the second healthcare professional 26'.

Figure 5A:
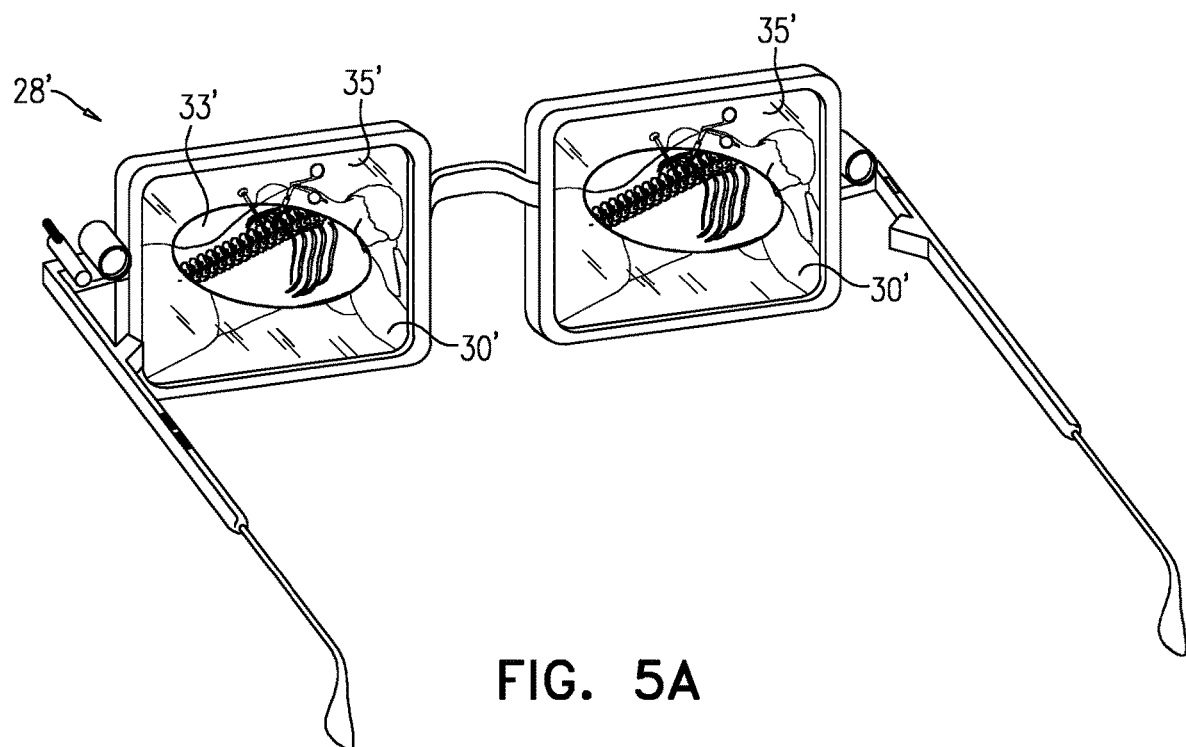
FIGS. 5A and 5B are schematic illustrations of examples of displays of head-mounted devices as worn by respective healthcare professionals, when the line of sight between a tracking device of one of the healthcare professionals with respect to a patient marker is at least partially blocked, in accordance with some applications of the present invention.
Figure 5B:
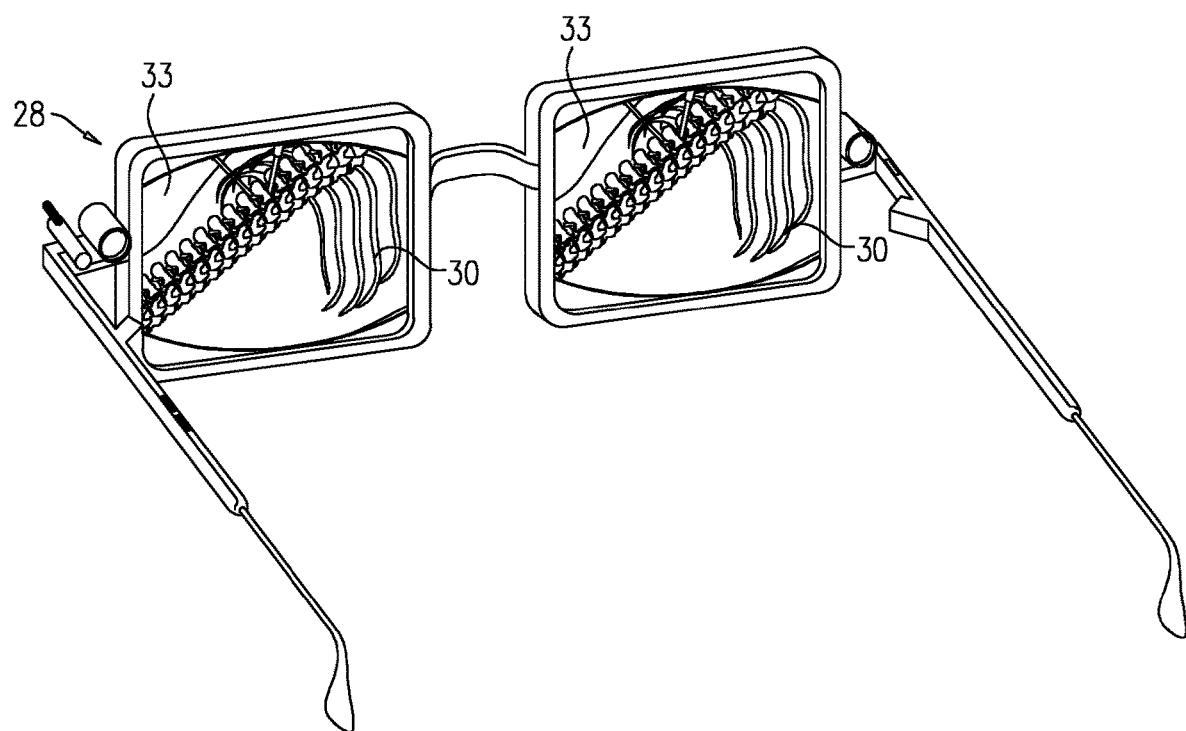

Reference is now made to FIGS. 5A and 5B, which are schematic illustration of examples of displays 30', 30 of head-mounted devices 28', 28 as worn by respective healthcare professionals 26', 26, when the line of sight between tracking device 34 of first healthcare professional 26 with respect to patient marker 38 is at least partially blocked, in accordance with some applications of the present invention. FIG. 5A shows an example of display 30' of second healthcare professional 26', who is shown on the right side of the patient in FIG. 1, and FIG. 5B shows an example of display 30 of first healthcare professional 26, who is shown on the left side of the patient in FIG. 1. For some applications, when the line of sight between tracking device 34 of first healthcare professional 26 with respect to patient marker 38 is at least partially blocked, the virtual image (of the tool and the anatomy) from the line of sight of the second healthcare professional is displayed, such that it fills substantially the whole head-mounted display 30 of the first healthcare professional, and the first healthcare professional is not be shown any of the actual patient anatomy via a transparent portion of the display. An example of such an embodiment is shown in FIGS. 5A and 5B, which show the virtual image from head-mounted displays 30' (shown in FIG. 5A) displayed within portion 33 of the head-mounted displays 30 of the first healthcare professional, and portion 33 filling substantially the whole of head-mounted displays 30 of the first healthcare professional (shown in FIG. 5B).

Figure 6A:
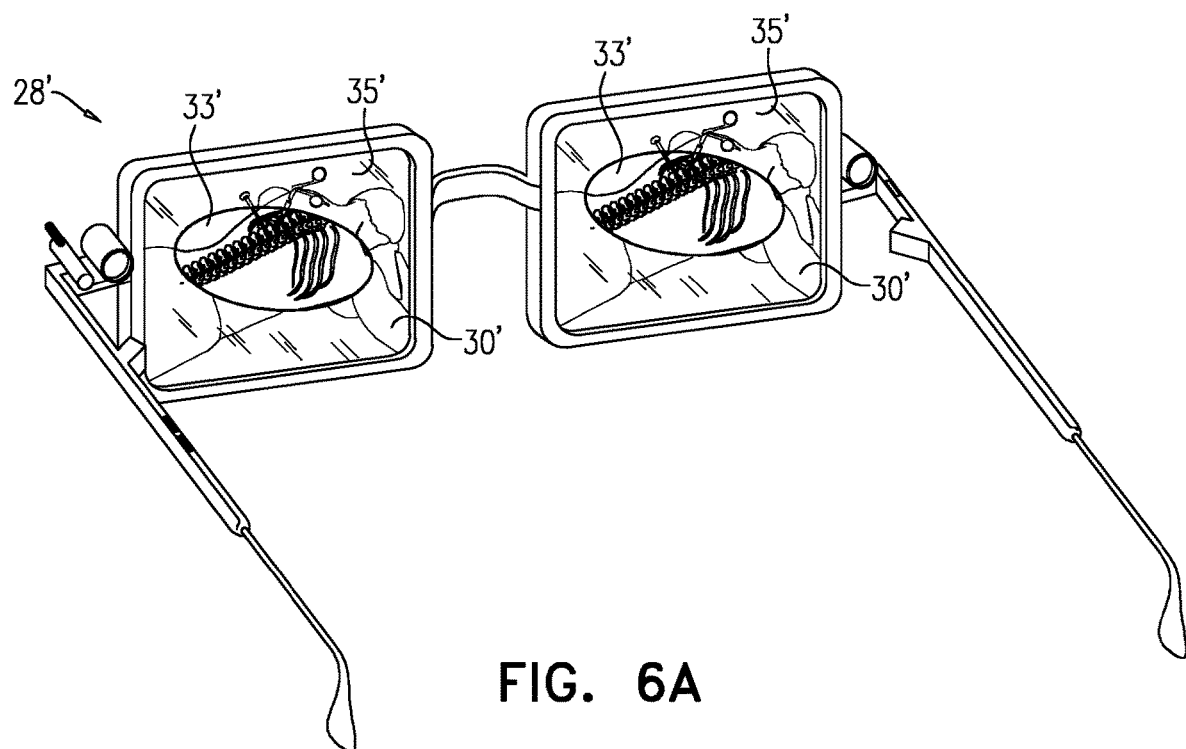
FIGS. 6A and 6B are schematic illustration of examples of displays of head-mounted devices as worn by respective healthcare professionals, when the line of sight between a tracking device of one of the healthcare professionals with respect to a patient marker is at least partially blocked, in accordance with some applications of the present invention.
Figure 6B:
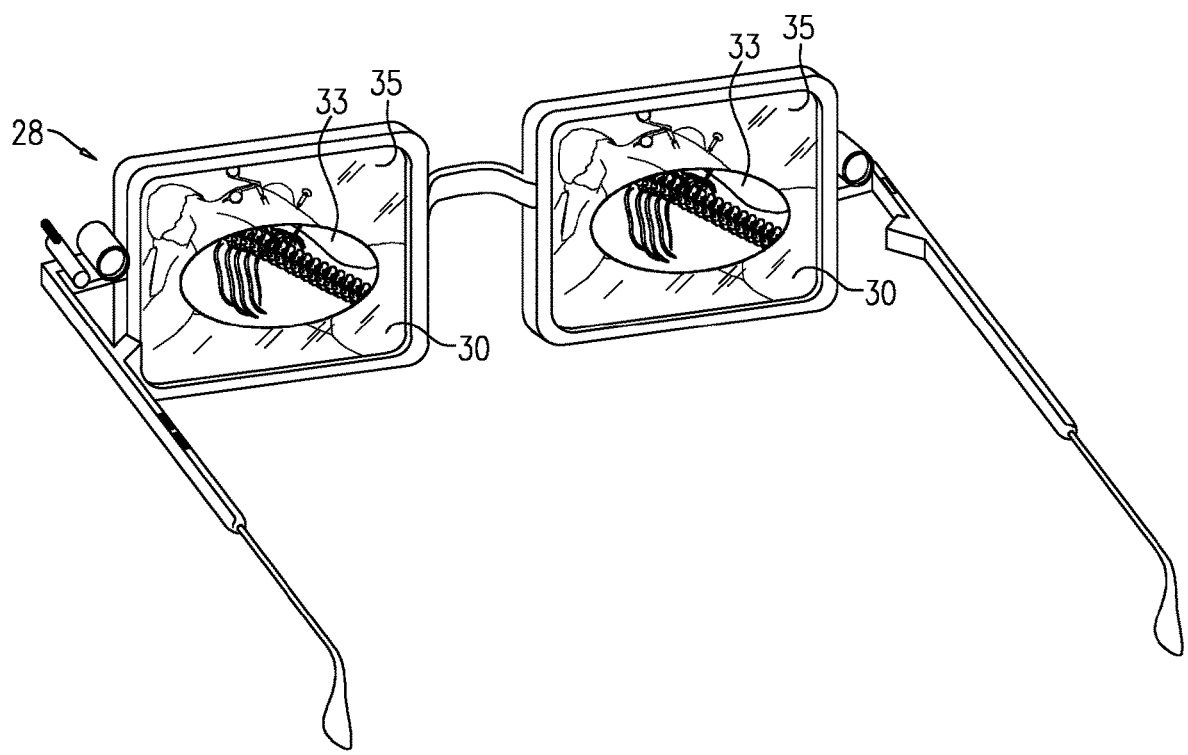

Reference is now made to FIGS. 6A and 6B, which are schematic illustration of examples of displays 30', 30 of head-mounted devices 28', 28 as worn by respective healthcare professionals 26', 26, when the line of sight between tracking device 34 of first healthcare professional 26 with respect to patient marker 38 is at least partially blocked, in accordance with some applications of the present invention. FIG. 6A shows an example of display 30' of second healthcare professional 26', who is shown on the right side of the patient in FIG. 1, and FIG. 6B shows an example of display 30 of first healthcare professional 26, who is shown on the left side of the patient in FIG. 1. For some applications, in response to detecting that tracking device 34 has lost its line of sight of the patient marker, such that the location and/or orientation of the head-mounted device relative to the patient cannot be determined to a given level of accuracy using tracking device 34, the computer processor generates an image of the virtual tool within the virtual anatomy of the subject, but without regard to aligning the computer-generated image with the actual patient anatomy. For some such applications, the virtual image that is generated in portion 33 of display 30 of the first healthcare professional continues to be shown from the first healthcare professional's previous known line of sight, but the position of the tool with respect to the anatomy is updated based upon data received from tracking device 34'. Second portion 35 of the display of the first healthcare professional is kept transparent such that the first healthcare professional sees the patient's anatomy from his/her own current line of sight. An example of such an embodiment is shown in FIGS. 6A and 6B. As shown in FIG. 6B, since changes in the location of head-mounted device 28 with respect to the patient marker are not tracked and accounted for, this may result in a slight misalignment of the virtual image (shown in portion 33) with respect to the patient's body (shown in portion 35). In this regard, it is noted that, in general, the first healthcare professional uses the virtual image of the tool overlaid upon the virtual image of the patient's anatomy, for navigation of the tool. As such, the healthcare professional is typically able to continue to navigate the tool, even though the virtual image of the tool and the patient's anatomy is not aligned with his/her view of the patient's anatomy.

For some applications, generally similar techniques to those described in the above paragraph are performed, but with the additional tracking data that is used for generating an image on head-mounted display 30 being received from tracking device 60, as an alternative to, or in addition to, being received from tracking device 34' of second head-mounted device 28'. For some applications, in response to detecting that tracking device 34 has lost its line of sight of the tool marker, such that the location and/or orientation of the tool with respect to the patient cannot be determined to a given level of accuracy, the computer processor determines the location of the tool relative to the patient, using data received from tracking device 34' and/or tracking device 60. Typically, a virtual image, which includes the virtual patient anatomy and the virtual tool shown at its current location, is displayed on head-mounted display 30' of head-mounted device 28, with the current location of the tool with respect to the patient having been determined based upon the data received from tracking device 34' and/or tracking device 60.

For some applications, the computer processor is configured to incorporate tracking data that is received from an additional tracking device (i.e., a tracking device in addition to tracking device 34) in order to generate an image upon head-mounted display 30 of first head-mounted device 28, even when the patient marker and the tool marker are within the line of sight of tracking device 34. For some applications, the computer processor determines the location of the tool with respect to the patient, using a combination of data received from tracking device 34' and data received from tracking device 34, and/or using a combination of data received from tracking device 60 and data received from tracking device 34. For example, the computer processor may determine an average (e.g., a mean) current location of the tool with respect to the patient, using the aforementioned combinations of received data, and the computer processor may the generate an image of a virtual tool on virtual anatomy upon head-mounted display 30, in which the tool is positioned at the determined current position.

For some applications, even if a portion of the tracking elements on the patient marker become obscured such that they are not within the line of sight of tracking device 34, the computer processor continue to track the location of the head-mounted device with respect to the patient by tracking the marker using a tracking algorithm (e.g., using a Kalman filter). Typically, in such cases, at least while the patient marker is partially obscured, the computer processor does not continue to actively identify the marker. Rather, the computer processor continues to track the already-identified marker using the aforementioned tracking algorithm. For some applications, if the patient marker becomes obscured (e.g., partially obscured or fully obscured) such that at least a portion of the patient marker is not within the line of sight of tracking device 34, the computer processor continues to determine the location of the patient relative to the head-mounted device, using inertial measurement unit 44, in combination with the last location of the patient marker as determined using data from tracking device 34.

Applications of the invention described herein can take the form of a computer program product accessible from a computer-usable or computer-readable medium (e.g., a non-transitory computer-readable medium) providing program code for use by or in connection with a computer or any instruction execution system, such as computer processor 32 and/or 45. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid-state memory, magnetic tape, a removable computer diskette, a random-access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor (e.g., computer processor 32 and/or 45) coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object-oriented programming language such as Java, Smalltalk, C++ or the like and conventional procedural programming languages, such as the C programming language or similar programming languages.

It will be understood that the algorithms described herein, can be implemented by computer program instructions. These computer program instructions may be provided to a processor of a general-purpose computer, special purpose computer, or other programmable data processing apparatus to produce a machine, such that the instructions, which execute via the processor of the computer (e.g., computer processor 32 and/or 45) or other programmable data processing apparatus, create means for implementing the functions/acts specified in the algorithms described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the algorithms. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the algorithms described in the present application.

Computer processor 32 and/or computer processor 45 is typically a hardware device programmed with computer program instructions to produce a special purpose computer. For example, when programmed to perform the algorithms described with reference to the figures, computer processor 32 and/or 45 typically acts as a special purpose image-generating computer processor. Typically, the operations described herein that are performed by computer processor 32 and/or 45 transform the physical state of a memory, which is a real physical article, to have a different magnetic polarity, electrical charge, or the like depending on the technology of the memory that is used. For some applications, operations that are described as being performed by a computer processor are performed by a plurality of computer processors in combination with each other.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A tracking system for image-guided surgery, the tracking system comprising:
   a first head-mounted device to be worn by a surgeon performing a surgical procedure, the first head-mounted device comprising a first display and a first tracking device that comprises a first camera;
   a patient marker comprising an array of elements configured to be visible to the first camera of the first tracking device to enable determination of a location and orientation of the first head-mounted device with respect to the patient marker;
   a second tracking device that is separate from the first head-mounted device, the second tracking device comprising a second camera,
   wherein the first camera and the second camera are each configured to capture images of at least a portion of a tool used in the surgical procedure; and
   at least one computer processor configured to:
      track a location and orientation of the tool with respect to the patient marker using data from the first tracking device;
      generate for display by the first display, using the tracked location and orientation of the tool, augmented reality images comprising a virtual image of the tool aligned with a virtual image of anatomy of a patient;
      detect that at least one of (i) a line of sight between the first tracking device and the patient marker is blocked and a line of sight between the first tracking device and the tool is not blocked, or (ii) a line of sight between the first tracking device and the tool is blocked and a line of sight between the first tracking device and the patient marker is not blocked; and
      in response to the detection:
         track the location and orientation of the tool with respect to the patient marker using data from the second tracking device; and
         generate for display by the first display, using the tracked location and orientation of the tool using the data from the second tracking device, augmented reality images comprising a virtual image of the tool aligned with a virtual image of anatomy of a patient.

2. The tracking system of claim 1, further comprising a second head-mounted, the second head-mounted device comprising a second display and the second tracking device.

3. The tracking system of claim 2, wherein the at least one computer processor is further configured to generate augmented reality images for display by the second display.

4. The tracking system of claim 1, wherein the second tracking device is disposed in a stationary position.

5. The tracking system of claim 1, wherein the tool comprises a tool marker, and wherein the first camera and the second camera are each configured to capture images of at least the tool marker of the tool.

6. The tracking system of claim 1, wherein the first tracking device further comprises a light source.

7. The tracking system of claim 1, wherein the first head-mounted device comprises the at least one computer processor.

8. The tracking system of claim 1, wherein the at least one computer processor is disposed externally to the first head-mounted device.

9. The tracking system of claim 1, wherein the at least one computer processor is further configured to:
   in the augmented reality images generated in response to detecting that the line of sight between the first tracking device and the patient marker is blocked, position the virtual image of the anatomy of the patient based upon data from tracking of the patient marker by the first tracking device at a time when the line of sight between the first tracking device and the patient marker was not blocked.

10. The tracking system of claim 1, wherein the first head-mounted device further comprises an inertial measurement unit, and wherein the at least one computer processor is further configured to:
   in the augmented reality images generated in response to detecting that the line of sight between the first tracking device and the patient marker is blocked, position the virtual image of the anatomy of the patient based upon data from tracking of movements of the first head-mounted device using the inertial measurement unit.

11. The tracking system of claim 1, wherein the detection comprises detecting that the line of sight between the first tracking device and the patient marker is blocked and the line of sight between the first tracking device and the tool is not blocked.

12. The tracking system of claim 1, wherein the detection comprises detecting that the line of sight between the first tracking device and the tool is blocked and the line of sight between the first tracking device and the patient marker is not blocked.

13. A tracking system for image-guided surgery, the tracking system comprising:
   a first head-mounted device to be worn by a surgeon performing a surgical procedure, the first head-mounted device comprising a first display and a first tracking device that comprises a first camera;
   a patient marker comprising an array of elements configured to be visible to the first camera of the first tracking device to enable determination of a location and orientation of the first head-mounted device with respect to the patient marker;
   a second tracking device that is separate from the first head-mounted device, the second tracking device comprising a second camera,
   wherein the first camera and the second camera are each configured to capture images of at least a portion of a tool used in the surgical procedure; and
   at least one computer processor configured to:
      track a location and orientation of the first head-mounted device with respect to the patient marker using data from the first tracking device;
      track a location and orientation of the tool with respect to the patient marker using data from the first tracking device;
      generate, for display by the first display, augmented reality images comprising a virtual image of the tool aligned with a virtual image of the anatomy of the patient, the augmented reality images being aligned with actual patient anatomy based upon the tracking of the location and orientation of the first head-mounted device with respect to the patient marker;
      detect that the line of sight between the first tracking device and the patient marker is blocked and the line of sight between the first tracking device and the tool is not blocked; and in response to the detection:

track the location and orientation of the tool with respect to the patient marker using data from the second tracking device; and generate, for display by the first display, augmented reality images comprising a virtual image of the tool aligned with a virtual image of the anatomy of the patient, the augmented reality images being aligned with actual patient anatomy.

14. The tracking system of claim 13, wherein first head-mounted device further comprises an inertial measurement unit, and wherein the augmented reality images generated in response to the detection are aligned with actual patient anatomy based upon data from tracking of movements of the first head-mounted device using the inertial measurement unit of the first head-mounted device.

15. The tracking system of claim 13, further comprising a second head-mounted, the second head-mounted device comprising a second display and the second tracking device.

16. The tracking system of claim 15, wherein the at least one computer processor is further configured to generate augmented reality images for display by the second display.

17. The tracking system of claim 13, wherein the second tracking device is disposed in a stationary position.

18. The tracking system of claim 13, wherein the tool comprises a tool marker, and wherein the first camera and the second camera are each configured to capture images of at least the tool marker of the tool.

19. The tracking system of claim 13, wherein the first tracking device further comprises a light source.

20. The tracking system of claim 13, wherein the at least one computer processor is integrated within the first head-mounted device.

* * * * *